(12) United States Patent
Nordman et al.

(10) Patent No.: US 7,468,793 B2
(45) Date of Patent: Dec. 23, 2008

(54) TIME-DELAY INTEGRATION IN ELECTROPHORETIC DETECTION SYSTEMS

(75) Inventors: Eric S. Nordman, Palo Alto, CA (US); Richard T. Reel, Hayward, CA (US); John S. Shigeura, Portola Valley, CA (US)

(73) Assignee: Applied Biosystems Inc., Foster City, CA (US)

( * ) Notice: Subject to any disclaimer, the term of this patent is extended or adjusted under 35 U.S.C. 154(b) by 0 days.

(21) Appl. No.: 11/012,664

(22) Filed: Dec. 15, 2004

(65) Prior Publication Data

US 2005/0213093 A1 Sep. 29, 2005

Related U.S. Application Data

(62) Division of application No. 10/205,028, filed on Jul. 25, 2002, now Pat. No. 6,856,390.

(51) Int. Cl.
*G01N 21/00* (2006.01)
(52) U.S. Cl. ...................................... 356/344
(58) Field of Classification Search ........................ None
See application file for complete search history.

(56) References Cited

U.S. PATENT DOCUMENTS

| | | | |
|---|---|---|---|
| 4,832,815 A | 5/1989 | Kambara et al. | |
| 4,833,332 A | 5/1989 | Robertson et al. | |
| 4,931,223 A | 6/1990 | Bronstein et al. | |
| 5,091,652 A | 2/1992 | Mathies et al. | |
| 5,141,609 A | 8/1992 | Sweedler et al. | |
| 5,173,748 A * | 12/1992 | Bilhorn ...................... | 356/328 |
| 5,188,934 A | 2/1993 | Menchen et al. | |
| 5,192,412 A | 3/1993 | Kambara et al. | |
| 5,268,080 A | 12/1993 | Kambara et al. | |
| 5,277,780 A | 1/1994 | Kambara | |
| 5,314,602 A | 5/1994 | Kambara et al. | |
| 5,366,608 A | 11/1994 | Kambara | |
| 5,388,860 A | 2/1995 | Brede et al. | |

(Continued)

FOREIGN PATENT DOCUMENTS

EP 0 616 211 9/1994

(Continued)

OTHER PUBLICATIONS

European Search Report, mailed Dec. 14, 2004, for European Application No. 02 75 6697 (3 pages).

(Continued)

*Primary Examiner*—Michael P Stafira
(74) *Attorney, Agent, or Firm*—Kilyk & Bowersox, P.L.L.C.

(57) ABSTRACT

An apparatus for detecting analytes in a sample is provided. The apparatus includes: one or more channels having a detection zone; one or more irradiation sources disposed for irradiating the detection zone with non-coherent radiation; a detector array disposed for collecting light signals emitted from markers in the detection zone excited by the radiation, the detector array having an output; and a system coupled to the detector array for effecting time delay integration of the charges on the detector array corresponding to the light signals by accumulating the charges before reading the charges at the output of the detector array. Other apparatus and methods for detecting analytes in a sample are also provided.

32 Claims, 8 Drawing Sheets

U.S. PATENT DOCUMENTS

| | | |
|---|---|---|
| 5,439,578 A | 8/1995 | Dovichi et al. |
| 5,470,710 A | 11/1995 | Weiss et al. |
| 5,529,679 A | 6/1996 | Takahashi et al. |
| 5,582,705 A | 12/1996 | Yeung et al. |
| 5,627,643 A | 5/1997 | Birnbaum et al. |
| 5,636,017 A | 6/1997 | Bruno et al. |
| 5,667,656 A | 9/1997 | Kambara |
| 5,674,442 A | 10/1997 | Morita |
| 5,675,155 A | 10/1997 | Pentoney et al. |
| 5,695,626 A | 12/1997 | Yeung et al. |
| 5,710,628 A | 1/1998 | Waterhouse et al. |
| 5,717,602 A | 2/1998 | Kenning |
| 5,730,850 A | 3/1998 | Kambara et al. |
| 5,741,411 A | 4/1998 | Yeung et al. |
| 5,741,412 A | 4/1998 | Dovichi et al. |
| 5,754,291 A | 5/1998 | Kain |
| 5,784,157 A | 7/1998 | Gorfinkel et al. |
| 5,790,727 A | 8/1998 | Dhadwal et al. |
| 5,833,826 A | 11/1998 | Nordman |
| 5,833,827 A | 11/1998 | Anazawa et al. |
| 5,847,162 A | 12/1998 | Lee et al. |
| 5,885,778 A | 3/1999 | Menchen et al. |
| 5,936,087 A | 8/1999 | Benson et al. |
| 6,005,663 A | 12/1999 | Waterhouse et al. |
| 6,008,379 A | 12/1999 | Benson et al. |
| 6,017,434 A | 1/2000 | Simpson et al. |
| 6,020,481 A | 2/2000 | Benson et al. |
| 6,025,505 A | 2/2000 | Lee et al. |
| 6,051,719 A | 4/2000 | Benson et al. |
| 6,084,667 A | 7/2000 | Melman et al. |
| 6,110,683 A | 8/2000 | Reynolds et al. |
| 6,140,048 A | 10/2000 | Müller et al. |
| 6,249,341 B1 | 6/2001 | Basiji et al. |
| 6,404,495 B1 | 6/2002 | Melman et al. |
| 6,529,275 B2 | 3/2003 | Amirkhanian et al. |
| 6,690,467 B1 | 2/2004 | Reel |

FOREIGN PATENT DOCUMENTS

| | | |
|---|---|---|
| WO | WO 88/04777 | 6/1988 |
| WO | WO 95/11961 | 5/1995 |
| WO | WO 95/23348 | 8/1995 |
| WO | WO 97/19342 | 5/1997 |
| WO | WO 97/45539 | 12/1997 |
| WO | WO 98/12536 | 3/1998 |
| WO | WO 00/25113 | 5/2000 |

OTHER PUBLICATIONS

Altria, Capillary electrophoresis, *Royal Society of Chemistry*, 7 Sheets, (2000).

Brochure, Charge-Coupled Devices for Quantitative Electronic Imaging, *Photometrics, Ltd*, pp. 1-3, and 6-17, (1992).

Bronstein, *Anal. Biochemistry*, 219:169-81 (1993).

*Charge-Coupled Devices for Quantitative Electronic Imaging*, Photometrics Ltd., (1992).

Genome Sequencing Center, Washington University School of Medicine St. Louis, MO USA, *EST & GSS Projects*, http://genome.wustl.edu/est/est_general/trace_intro.html., (Monday, Mar. 26, 2001).

Grossman, Factors Affecting the Performance of Capillary Electrophoresis Separations: Joule Heating, Electroosmosis, and Zone Dispersion, *Academic Press, Inc,*, pp. 3, 24, 28, and 38, (1992).

Karger et al., Multiwavelength fluorescence detection for DNA sequencing using capillary electrophoresis, *Nucleic Acids Research*, vol. 19, No. 18, pp. 4955-4962, (Jul. 29, 1991).

Kostichka et al., High Speed Automated DNA Sequencing in Ultrathin Slab Gels, *Bio/Technology*, vol. 10, pp. 78-81, (Jan. 1992).

Kricka, Nonisotopic DNA Probe Techniques, *Academic Press*, San Diego, pp. 3-28, (1992).

Novotny, Capillary electrophoresis, *Current Opinion in Biotechnology*, vol. 7, pp. 29-34 (1996).

Reel, *Camera Lens Spectrograph Optics Design for MegaGUT*, pp. 1-42, (Jan. 16, 1997).

Ross et al., High Sensitivity is Key to CE Detection Boost, *Today's Chemist at Work*, Vo. 6(8), pp. 31-32, 34 and 36, (Sep. 1997).

Sanger et al., DNA Sequencing with Chain Terminating Inhibitors, 74 *Proc. Nat. Acad. Sci. USA*, 5463, (1977).

Simpson et al., A transmission imaging spectrograph and microfabricated channel system for DNA analysis, *Electrophoresis 2000*, vol. 21, pp. 135-149 (2000).

Smith et al., Fluorescence detection in automated DNA sequence analysis, 321 *Nature* 674, (1986).

Smith et al., The Future of DNA sequencing, 262 *Science* 530, (1993).

Sweedler et al., Fluorescence Detection in Capillary Zone Electrophoresis Using a Charge-Coupled Device with Time-Delayed Integration, *Analytical Chemistry*, vol. 63, No. 5, pp. 496-502, (Mar. 1, 1991).

\* cited by examiner

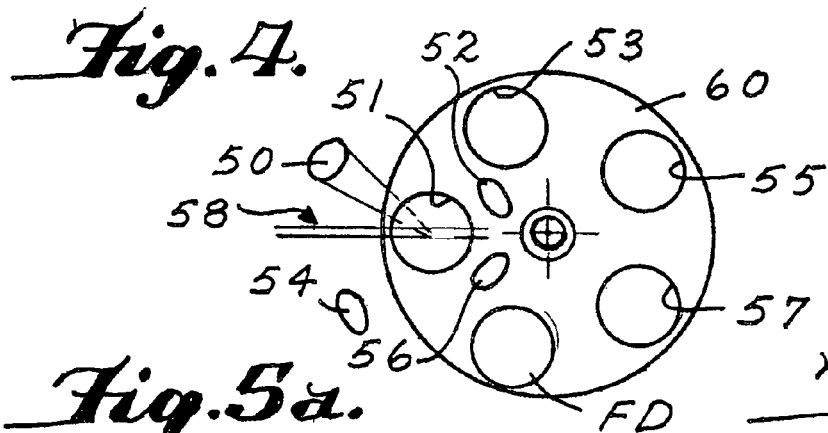
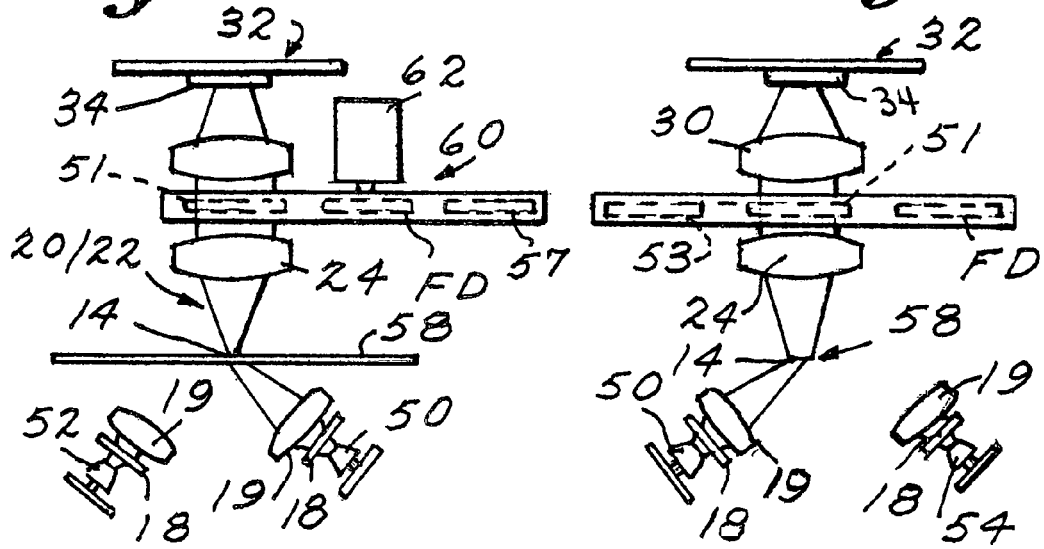
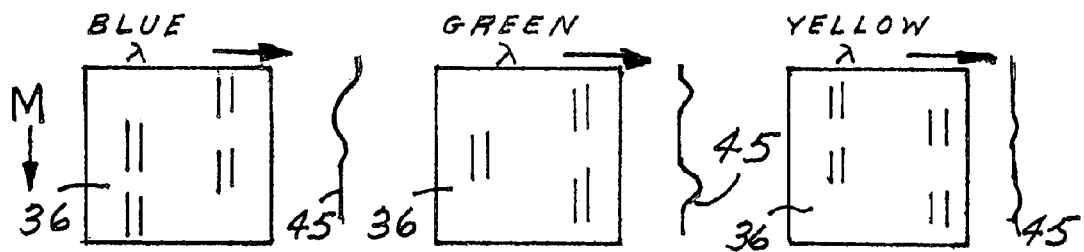
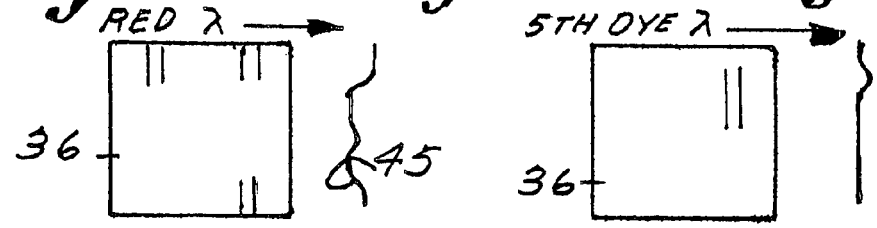

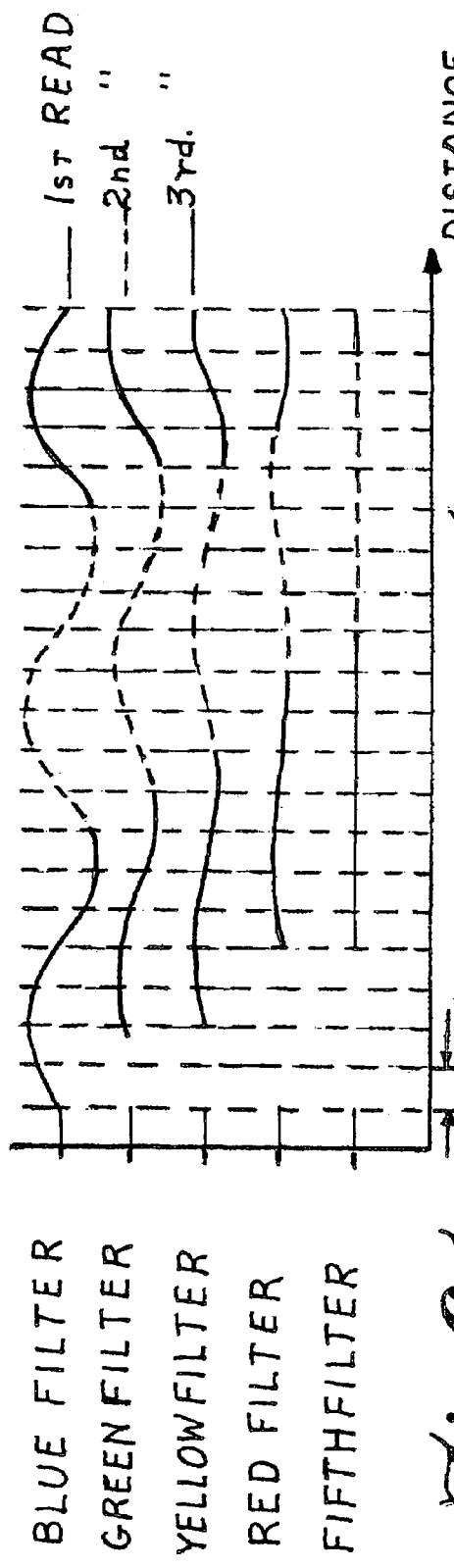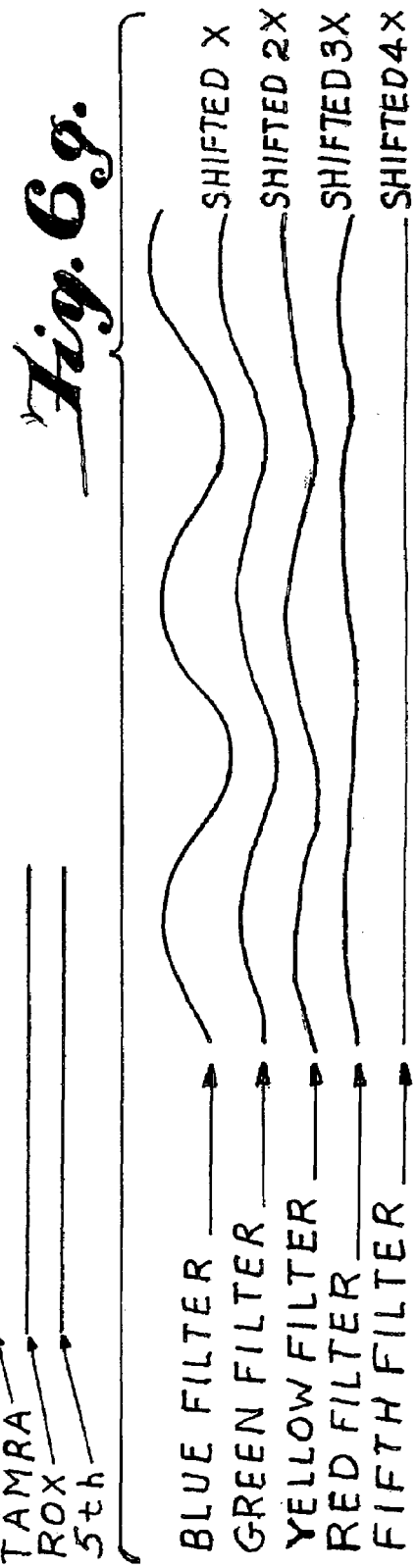

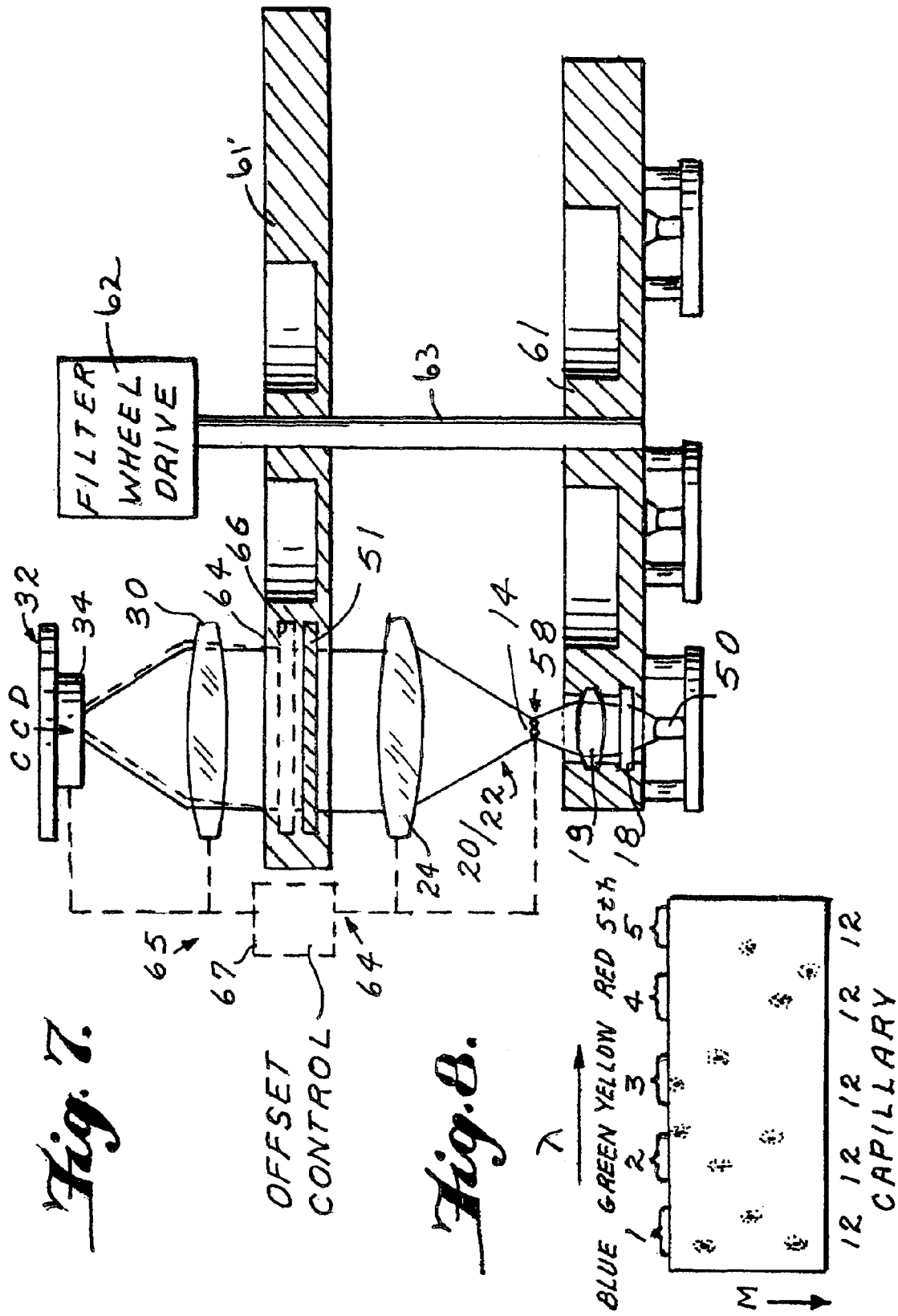

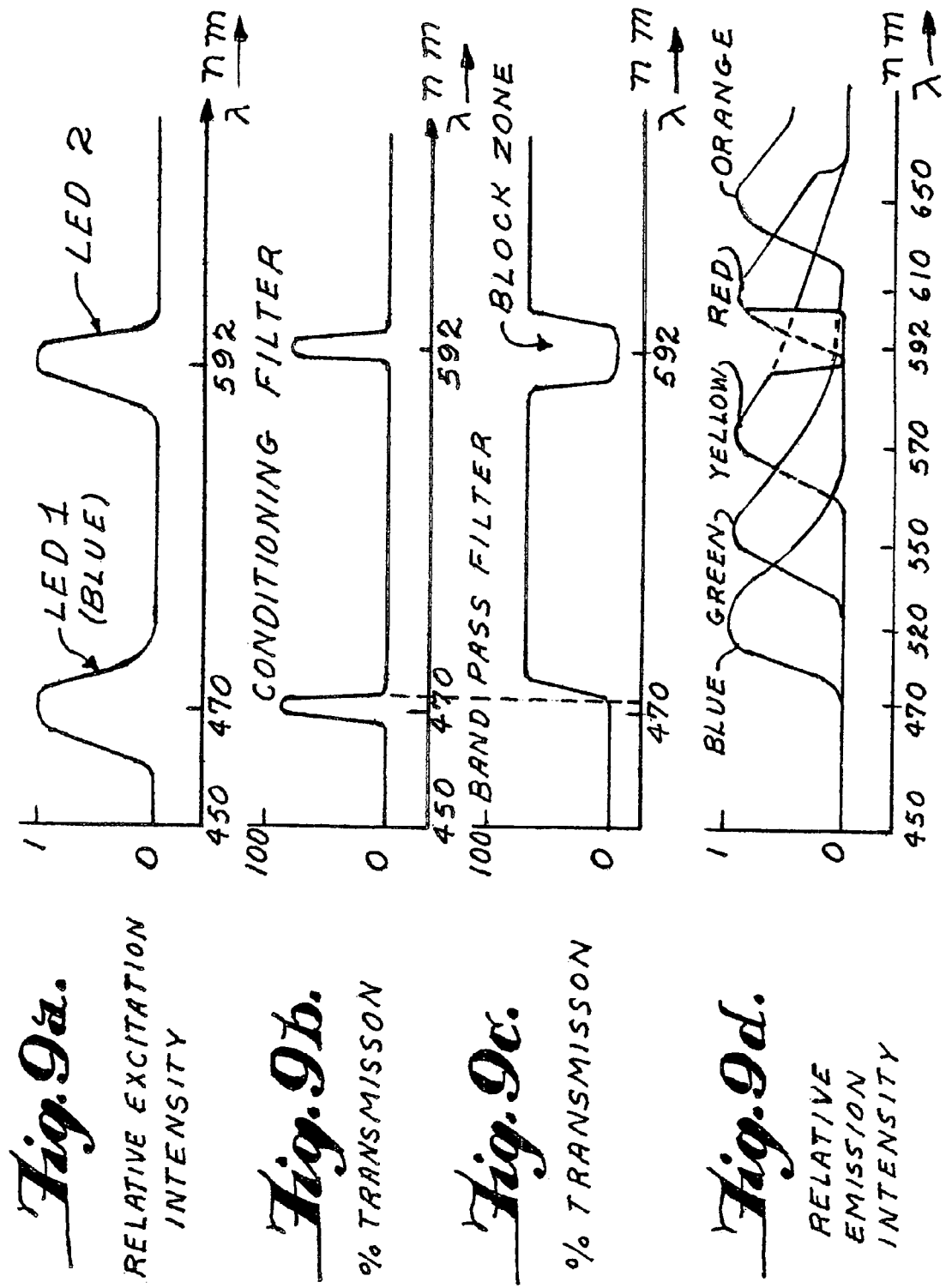

TIME-DELAY INTEGRATION IN ELECTROPHORETIC DETECTION SYSTEMS

PRIORITY AND RELATED APPLICATIONS

This application is a divisional application of U.S. patent application Ser. No. 10/205,028, filed Jul. 25, 2002, which is incorporated herein in its entirety by reference.

FIELD

The various embodiments relate to electrophoretic detection systems, and, in particular, to arrangements and methods for light detection during electrophoresis.

INTRODUCTION

Well-known examples of biopolymer analysis using DNA sequencing are taught, for example, in F. Sanger, et. al., *DNA Sequencing with Chain Terminating Inhibitors,* 74 Proc. Nat. Acad. Sci. USA 5463 (1977); Lloyd M. Smith, et. al., *Fluorescence detection in automated DNA sequence analysis,* 321 Nature 674 (1986); Lloyd M. Smith, *The Future of DNA Sequencing,* 262 Science 530 (1993). These and all other publications and patents cited herein are incorporated herein in their entireties by reference.

Known capillary electrophoresis systems and methods can require laser-induced fluorescence for exciting marker compounds or markers, such as dye molecules typically used to label analytes. Unfortunately, laser apparatuses are expensive to use, energy inefficient, consume large amounts of power, and are physically large, rendering electrophoretic systems incorporating lasers cumbersome to use.

The use of sources of irradiation other than lasers for the excitation of marker compounds provides many advantages. Although the use of light emitting diodes (LED's) for generating fluorescence in dye molecules is taught, for example, in U.S. Pat. Nos. 6,005,663 and 5,710,628, the contents of which are incorporated herein in their entireties by reference, the use of LED's in such electrophoretic methods typically results in low signal strengths and detection sensitivity that is only marginal. The low signal strength tends to impair adequate detection of marker compounds.

Electrophoresis arrangements that employ complex optics causing a reduction of the collecting efficiency of the detector also result in low sensitivity. The low sensitivity is aggravated through the use of LED's, which compromise sensitivity in the first instance. The problem of lowered sensitivity through LED use is further exacerbated when using multiple-channel-type electrophoretic devices, that is, electrophoretic devices using an etched plate with capillary-sized grooves, or using a plurality of capillary tubes, where either type of device has multiple-channels used to increase throughput.

An electrophoretic apparatus and method that include a cost-effective and convenient source of irradiation and that do not compromise sensitivity or resolution would be desirable, especially in multiple-channel electrophoretic systems used to increase throughput.

SUMMARY

According to various embodiments, the present invention can relate to an apparatus and method for detecting components, for example, analytes, in a sample.

According to various embodiments, an apparatus is provided for detecting analytes in a sample. According to various embodiments, the apparatus can include: one or more channels having a detection zone; one or more irradiation sources disposed for irradiating the detection zone with non-coherent radiation; a detector array disposed for collecting light signals emitted from markers in the detection zone excited by the radiation, where the detector array can have an output; and a system coupled to the detector array for effecting time delay integration of the charges on the detector array corresponding to the light signals by accumulating the charges before reading the charges at the output of the detector array.

According to various embodiments, an apparatus is provided for detecting analytes in a sample, wherein the apparatus can include: one or more channels having a detection zone; one or more irradiation sources disposed for irradiating the detection zone with radiation; a detector array disposed for collecting light signals emitted from markers in the detection zone excited by the radiation, where the detector array can have an output; and a system coupled to the detector array for effecting time delay integration of the charges on the detector array corresponding to the light signals by accumulating the charges before reading the charges at the output of the detector array, wherein the system for effecting time delay integration can do so by moving, relative to one another, the detector array and light signals from the detection zone.

According to various embodiments, an apparatus for detecting analytes in a sample is provided, wherein the apparatus can include: one or more channels having a detection zone; one or more irradiation sources disposed for irradiating the detection zone with radiation; a detector array disposed for collecting light signals emitted from markers in the detection zone excited by the radiation, where the detector array can have an output; a system coupled to the detector array for effecting time delay integration of the charges on the detector array corresponding to the light signals by accumulating the charges before reading the charges at the output of the detector array; and a re-imaging lens disposed between the detection zone and the detector array for optically inverting an image produced by the light signals before the image is collected by the detector array.

According to various embodiments, an apparatus for detecting analytes in a sample is provided wherein the apparatus can comprise: a channel-defining member defining at least one channel therein having a detection zone; and a separating system coupled to the at least one channel for separating a sample containing analytes and disposed in contact with a migration medium disposed within the at least one channel into analyte bands migrating along the at least one channel, wherein each analyte band can be detectable by the presence of a corresponding marker. According to various embodiments, the apparatus can further include: at least one irradiation source for emitting non-coherent radiation and disposed for irradiating the detection zone of the at least one channel to thereby excite markers responsive to the radiation and which emit light signals indicative of corresponding analytes; a detector array disposed for collecting the light signals produced by the markers and for producing charges corresponding to the light signals, where the detector array can have an output; modulating optics for modulating light between the irradiation source and the detector array; and a time delay integration system for effecting, within the detector array, an accumulation of charges corresponding to light signals associated with at least one given analyte band before reading accumulated charges at the output of the detector array, the accumulation being effected during an integration time of the at least one given analyte band moving across the detection zone.

According to various embodiments, an apparatus is provided for detecting analytes in a sample, wherein the apparatus can include: a channel-defining member defining at least one channel therein having a detection zone; and a separating system coupled to the at least one channel for separating a sample containing analytes and disposed in contact with a migration medium in the at least one channel into analyte bands migrating along the at least one channel, wherein each analyte band can be detectable by the presence of a corresponding marker. According to various embodiments, the apparatus can further include at least one irradiation source disposed for irradiating the detection zone of the at least one channel with radiation to thereby excite markers responsive to the radiation and which emit light signals indicative of corresponding analytes; a detector array disposed for collecting the light signals produced by the markers and for producing charges corresponding to the light signals, where the detector array can have an output; modulating optics for modulating light between the at least one irradiation source and the detector array; and a time delay integration system for effecting, within the detector array, an accumulation of charges corresponding to light signals associated with at least one given analyte band before reading accumulated charges at the output of the detector array. The accumulation of charges can be effected during an integration time of the at least one given analyte band moving across the detection zone, by, for example, moving, relative to one another, the detector array and at least one of the detection zone and the modulating optics.

According to various embodiments, an apparatus is provided for detecting analytes in a sample, wherein the apparatus can include: a channel-defining member defining at least one channel therein having a detection zone; and a separating system coupled to the at least one channel for separating a sample containing analytes and disposed in contact with a migration medium in the at least one channel into analyte bands migrating along the at least one channel, wherein each analyte band can be detectable by the presence of a corresponding marker. The apparatus can further include at least one irradiation source disposed for irradiating the detection zone of the at least one channel with radiation to thereby excite markers responsive to the radiation for emitting light signals indicative of corresponding analytes. Together, the light signals can form an image corresponding to analyte bands migrating across the detection zone. The apparatus can also include a detector array disposed for collecting the light signals produced by the markers and for producing charges corresponding to the light signals, the detector array having an output; a re-imaging optical system disposed between the detection zone and the detector array for optically inverting an image produced by the light signals before the image is collected by the detector array; modulating optics for modulating light between the at least one irradiation source and the detector array; and a time delay integration system for effecting, within the detector array, an accumulation of charges corresponding to light signals associated with at least one given analyte band before reading accumulated charges at the output of the detector array, the accumulation being effected during an integration time of the at least one given analyte band moving across the detection zone.

Various embodiments can pertain to a method for detecting analytes in a sample, and can comprise the steps of: providing a channel-defining member defining at least one channel therein having a detection zone; providing migration medium within the at least one channel; separating a sample containing analytes and disposed in contact with the migration medium into analyte bands migrating along the at least one channel, wherein each analyte band can be detectable by the presence of a marker; irradiating the detection zone using at least one irradiation source providing non-coherent radiation that can thereby excite markers responsive to the radiation and that can emit light signals indicative of corresponding analytes; detecting the light signals produced by the markers by, for example, collecting the light signals on a detector array to produce charges on the detector array corresponding to the light signals; modulating light between the at least one irradiation source and the detector array; effecting a time delay integration of the light signals within the detector array by, for example, accumulating the charges within the detector array corresponding to light signals associated with at least one given analyte band during an integration time of the at least one given analyte band moving across the detection zone; and reading the accumulated charges.

Furthermore, according to various embodiments, an apparatus for detecting analytes in a sample is provided that can comprise: means defining at least one channel therein having a detection zone; means for separating a sample containing analytes and disposed in contact with a migration medium disposed within the at least one channel into analyte bands migrating along the at least one channel, wherein each analyte band can be detectable by the presence of a marker; means for irradiating the detection zone with non-coherent radiation, that can thereby excite markers responsive to the radiation and that can emit light signals indicative of corresponding analytes; means for detecting the light signals by collecting the light signals that can thereby produce charges corresponding thereto; means for effecting a time delay integration of the light signals within the detector array by, for example, accumulating within the detector array the charges corresponding to light signals associated with at least one given analyte band during an integration time of the at least one given analyte band moving across the detection zone; and means for reading the accumulated charges.

It is to be understood that both the foregoing general description and the following detailed description are exemplary and explanatory only. The accompanying drawings, which are incorporated in and constitute a part of this application, illustrate several exemplary embodiments and together with the instant description, serve to explain the principles of the present invention.

DRAWINGS

The skilled artisan will understand that the drawings described below, are for illustration purposes only. The drawings are not intended to limit the scope of the present teachings in any way.

FIG. 4 is a schematic, front-elevational view of an electrophoresis arrangement according to various embodiments for the sequential use of multiple-color irradiation sources along with filters on a filter wheel;

FIG. 5a is a schematic, top-plan view of the arrangement of FIG. 4;

FIG. 5b is a schematic, side-elevational view of the arrangement of FIG. 4;

FIGS. 6a through 6e are respective schematic views of images produced on the detector array of a detector, each image corresponding to light signals filtered through a respective filter on the filter wheel of FIG. 4;

FIG. 6f is a schematic representation of an electropherogram showing fluorescence intensity curves for each filter of the filter wheel in FIG. 4 during three signal readings by the detector;

FIG. 6g is a schematic representation of the intensity curves of FIG. 6f in aligned format for multicomponenting;

FIG. 6h is a schematic representation of multicomponented intensity curves for five different kinds of markers that can be used in the system of FIG. 4 based on the readings shown in FIG. 6f;

FIG. 7 is a top-plan, partially cross-sectional view of an electrophoresis arrangement according to various embodiments for the sequential use of multiple-color irradiation sources along with filters on a filter wheel and along with an offset system;

FIG. 8 is a schematic view of an image produced on the detector array of a detector using the arrangement of FIG. 7;

FIG. 9a is a graph of relative excitation intensity versus wavelength for a pair of LED's used in yet another embodiment of the present invention, the LED's being of different colors and being used to irradiate the detection zone simultaneously;

FIG. 9b is a graph showing percent transmission versus wavelength for a conditioning filter used to condition the light from the LED's of FIG. 9a;

FIG. 9c is a graph showing percent transmission versus wavelength for a bandpass filter used to filter through light signals produced by markers excited by the light from the LED's of FIG. 9a;

FIG. 9d is a graph showing relative emission intensity versus wavelength for the light filtered through the bandpass filter of FIG. 9c;

FIG. 12b is a graph showing percent integration per pixel throughout the width of the frame in shown in FIG. 12a.

DESCRIPTION

The apparatuses and methods herein can address the need for an electrophoresis device and process that employs a cost-effective and convenient source of irradiation. Various embodiments can be especially well suited for multiple-channel electrophoretic systems used to increase throughput.

Figure 1:
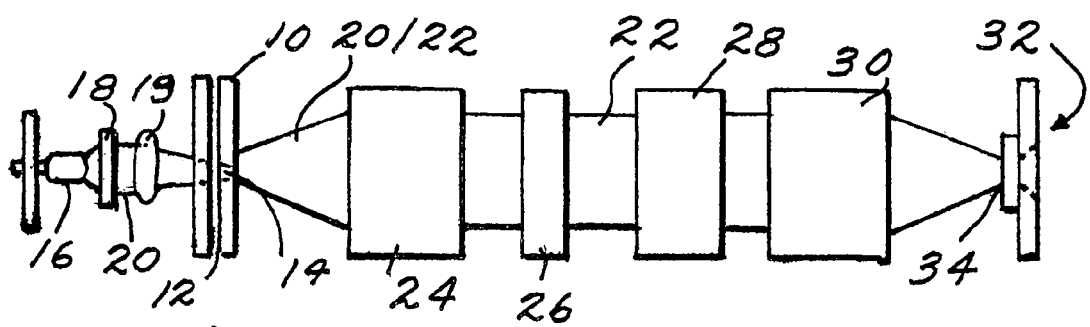
FIG. 1 is a schematic, side-elevational view of an electrophoresis arrangement according to various embodiments showing a channel-defining member in cross-section.

FIG. 1 shows an exemplary embodiment of an electrophoresis device. As depicted in FIG. 1, the arrangement can include a channel-defining member 10 defining a channel 12 therein for the migration of an analyte sample. The channel-defining member 10 may include a cover plate with or without grooves, an etched plate defining one or more capillary sized grooves therein, or one or more capillary tubes. According to various embodiments, the channel-defining member can be an etched plate having a plurality of channels or grooves, or the channel-defining member can include a plurality of capillary tubes. The use of a plurality of channels can allow a large number of analyte samples to be measured simultaneously in order to increase throughput. As is well known, for electrophoresis to occur, opposing ends of channel-defining member 10, such as an electrophoretic plate or capillary tube, can be placed in contact with corresponding electrodes connected to a power supply for generating an electric field across the plate or tube. This field can cause the analyte to migrate from a loading site (not shown) for the plate or tube arrangement of the channel-defining member 10, toward a detection site or detection zone 14. The detection zone can encompass that zone on the channel that is irradiated by an irradiation source to excite markers, such as dye markers, used to label analytes in the sample.

An example of a marker compound is a dye marker. Any suitable marker, such as, for example, a fluorophore, can be used. Fluorophores useful according various embodiments can include those that can be coupled to organic molecules, particularly proteins and nucleic acids, and that can emit a detectable amount of radiation or light signal in response to excitation by an available excitation source. Suitable markers can encompass materials having fluorescent, phosphorescent, and/or other electromagnetic radiation emissions. Irradiation of the markers can cause them to emit light at varying frequencies depending on the type of marker used.

One class of markers provides signals for the detection of labeled extension and amplification products by fluorescence, chemiluminescence, and electrochemical luminescence (Kricka, L. in *Nonisotopic DNA Probe Techniques*, Academic Press, San Diego, pp. 3-28 (1992)). Chemiluminescent labels include 1,2-dioxetane compounds (U.S. Pat. No. 4,931,223; and Bronstein, Anal. Biochemistry 219:169-81 (1994)). Fluorescent dyes useful for labeling probes, primers, and nucleotide 5'-triphosphates include fluoresceins, rhodamines (U.S. Pat. Nos. 5,366,860; 5,936,087; and 6,051, 719), cyanines (Kubista, WO 97/45539), and metal porphyrin complexes (Stanton, WO 88/04777). Fluorescent reporter dyes include xanthene compounds such as fluoresceins I and rhodamines II:

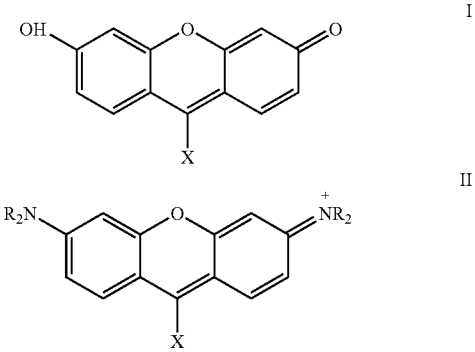

The ring positions of I and II above may be substituted. The amino R groups of II may be substituted. The substituents can include covalent attachments to the primers, probes and nucleotides. Examples of I and II formulae include wherein X can be phenyl substituted with carboxyl, chloro, and other groups, for example, as described in U.S. Pat. Nos. 5,847,162; 6,025,505; 5,674,442; 5,188,934; 5,885,778; 6,008,379; 6,020,481; and 5,936,087, which are incorporated herein in their entireties by reference, and wherein X can be hydrogen, for example, as described in U.S. Pat. No. 6,051,719, which is incorporated herein in its entirety by reference.

In the embodiment shown in FIG. 1, an irradiation source is provided that emits non-coherent light in a given frequency range, such as, for example, a light emitting diode (LED) 16. It is to be noted that, in the instant description, a source of non-coherent light can be a source emitting light that does not encompass laser light. According to various embodiments, the non-coherent light can have a frequency of about 660 nm or lower.

According to various embodiments, the light from the LED can be modulated by an excitation modulating optics system before reaching the detector zone 14. The excitation modulating optics system can include, as shown, a conditioning filter 18, the role of which can be to substantially block predetermined ranges of wavelengths of light emitted by the LED. The predetermined ranges can correspond to wavelengths of light that can overlap with the emission spectra of the markers being used. According to various embodiments, the conditioning filter may let through only light in the wavelength range of excitation light for one or more of the markers. Typically, any given LED emits excitation light in a spectral range. The range of wavelengths of the excitation light in turn may typically excite markers to emit light signals within a given spectral range in the detection zone. For the detection of light signals from the detection zone, one can block out that portion of the excitation light that would be in the same wavelength range as some or all of the light signals emitted from the detection zone. Otherwise, it can be difficult to determine which portion of the detected light is merely excitation light from the LED. The light passing through the conditioning filter 18 is conditioned light 20, as seen in FIG. 1. The excitation modulating optic can further include a focusing optical system 19. The conditioned light 20 can thereafter be focused by focusing optical system 19 for irradiating the analyte sample and corresponding markers in the detection zone 14. The thus irradiated marker or markers in turn emit light signals, such as through fluorescence, at frequencies specific to the irradiated marker, so as to present a peak intensity. For example, a dye excited by yellow light might have a fluorescence emission peak intensity at 610 nm corresponding to the orange portion of the spectrum, while a peak at about 460 nm is associated with the blue portion of the spectrum, and a peak at about 660 nm is associated with the red portion of the spectrum. It is noted that there are only a limited number of colors possible for efficient laser irradiation sources when compared with possible colors for efficient, non-coherent irradiation sources, such as LED's. The use of irradiation sources emitting non-coherent radiation in turn allows the use of a wider range of markers when compared with the use of lasers. By way of example, ROX, a known dye marker, is best excited at 590 nm. No laser, however, is particularly efficient at 590 nm. ROX is better excited by an LED emitting radiation at 590 nm.

The device of FIG. 1 further includes a collection modulating optics system that can include a collimating optical system 24, a wide bandpass filter 26, a transmission grating 28, and a re-imaging optical system 30. Emitted light 22 from the detection zone 14, and, in addition, conditioned light 20 passing through the detection zone 14, are collimated by a first optical component or system 24. In this respect, it is to be noted that the light from the detection zone includes the emitted light 22 and a portion of the conditioned light 20 passing through the detection zone. Alternatively, the excitation light can be brought in at an angle with respect to the detection zone such that most of the conditioned light passing through the detection zone is not collected by the collimating optical system 24. This reduces the excitation light that must be rejected. However, such an alternative arrangement also decreases the level of excitation light that hits the detection zone 14. It is, nevertheless, possible to establish a compromise between irradiation angle and level of excitation light, as readily recognizable by one skilled in the art.

The light 20 and 22 from the detection zone 14 can be collimated by collimating optical system 24. By collimation, what is meant in the context of various embodiments is any reduction in the propagation angle of the light being collimated. According to various embodiments, the reduction in the propagation angle of the light being collimated can result in a propagation angle between about 20 degrees and about 0 degrees.

According to various embodiments, a long pass filter, or, in the alternative, a wide bandpass filter, indicated by reference numeral 26, can thereafter be used for letting through, substantially exclusively, predetermined wavelengths of light from the detection zone corresponding to a portion of wavelengths of the light signals emitted by an associated marker. The portion of the wavelengths of the light signals can include, for example, all of the light signals, or it can include, for each marker, a range of wavelengths of the light signals, such as a range of wavelengths about the peak intensity of the light signals. As an example, a wide bandpass filter can block wavelengths of light outside of the range of from about 500 nm to about 700 nm, thereby letting through only light that corresponds very specifically to the light emitted by the markers, that is, corresponding to emitted light 22. Thereafter, emitted light 22 can be spectrally distributed by a transmission grating 28 and refocused by re-imaging optical system 30 onto an array 34 of solid-state detectors, or detector array 34. The excitation modulating optics system and the collection modulating optics system are hereinafter collectively referred to as "the modulating optics system" or "modulating optics". According to various embodiments, the array of solid-state detectors can include the photo-detecting surface of the parallel register of a charge-coupled device (CCD) 32. In the shown embodiment, the image produced by a refocusing of emitted light 22 is projected onto the detector array 34 of the CCD, producing a pattern of charge in proportion to the total integrated flux incident on each pixel of the parallel register, as is well known in the art.

Figure 2:
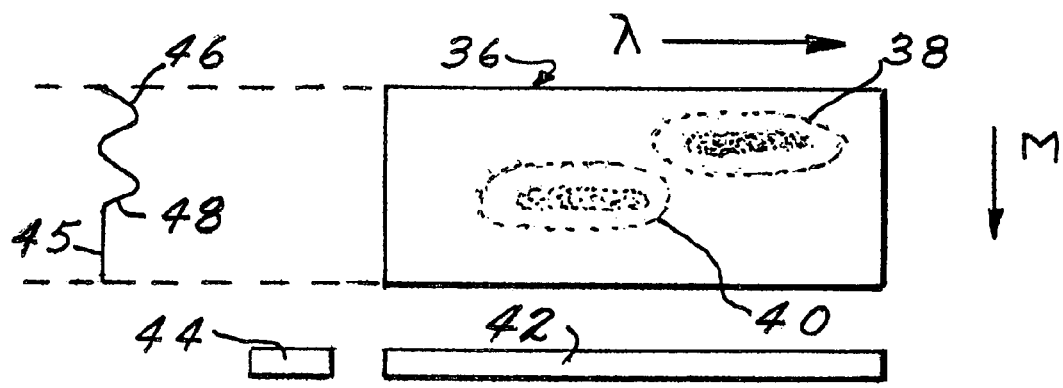
FIG. 2 is a schematic view of the image produced on the detector array of a detector at a time t using the arrangement of FIG. 1.
Figure 3:
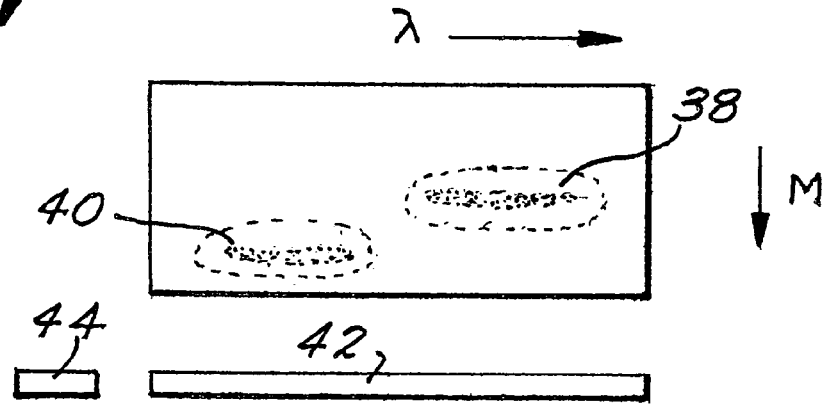
FIG. 3 is a view similar to FIG. 2 showing the image at a time $t+\Delta t$.

Referring additionally now to FIGS. 2 and 3, an image produced by moving analyte bands is recorded by the photo-detecting surface of CCD 32 (FIG. 1) at times t (FIG. 2) and t+Δt (FIG. 3). The photo-detecting surface 36 can be, according to an embodiment, part of the two dimensional detector array 34 shown above with respect to FIG. 1. Photo-detecting surface 36 can include a spectral axis as indicated by arrow λ on the figure, and a spatial axis along which the analyte bands move, as indicated by arrow M in FIGS. 2 and 3. As further seen in FIG. 2, the image created by the light signals emitted by excited markers produces two bands 38 and 40 on photo-detecting surface 36 substantially in the red and blue regions of the spectrum, respectively, each band corresponding to a marker used to label, for example, a predetermined type of analyte. The bands are spectrally distributed along the spectral axis by transmission grating 28 in FIG. 1. At time t, as shown in FIG. 2, the charges produced on surface 36 present two respective peaks 46 and 48 on intensity profile 45. These peaks correspond to bands 38 and 40, respectively. As seen in FIG. 3, at time t+Δt, both bands 38 and 40 have moved downward along the direction of migration M on the photo-detecting surface 36. Serial register 42 of the CCD 32 (FIG. 1) collects the charges accumulated for each analyte band during its integration time. All signals received from the detector can be converted from analog to digital and conveyed to a serial port for transmission to a multipurpose computer for storage and for further processing and analysis. The analog output can alternatively or additionally be sent directly to an output device for display or printing, or used for other purposes.

According to various embodiments, for example, as shown in the embodiment above, collection of the image is performed using time delay integration (TDI). In the CCD, the photogenerated charge in the photoactive elements or pixels can be transferred toward the serial register 42 one row at a time. The charge information in the serial row is then read by using a corresponding single on-chip amplifier or readout register 44 of the CCD. By way of example, for a 256×256 element CCD, each time a single imaging area is transferred to the serial register 42, 256 readouts of the thus transferred area are performed, each readout corresponding to a different spectral element. The above process continues until all 256 rows have been read 256 times.

Under a normal read-out approach, the motion of the images on the detector array 34 produces a blur. In TDI, according to various embodiments, the shutter is eliminated and the shifting of rows of the CCD is synchronized to the migration of the band of analyte in the channel. Thus, as an analyte band enters the excitation zone of the LED (detection zone 14), the light signals emitted therefrom are collected and illuminate the first row of the CCD, and the charge information is read using the CCD's amplifier or readout register 44. The band takes a period of time, $\Delta t_p$, to migrate on the channel so that its image migrates to the next row of the CCD, one row closer to the serial register. After this time period, the charge on the CCD can be shifted one row closer to the serial register, such that the fluorescence from the analyte still corresponds to the same charge information on the CCD. Therefore, distinct from the physical rows of the CCD, there exists in TDI according to various embodiments a continuously moving row of accumulating photogenerated charge. An example of TDI in a CE system using LIF is disclosed in U.S. Pat. No. 5,141,609 to Sweedler et al., and in J. F. Sweedler et al., Fluorescence Detection in Capillary Zone Electrophoresis Using a Charge-Coupled Device with Time Delayed Integration, Anal. Chem. 63, 496-502 (1991), the contents of both of which are incorporated herein in their entireties by reference. The effective integration time for a given analyte band can vary according to various embodiments from application to application. The effective integration time of a given analyte band can correspond to a time where the portion of the wavelengths of the light signals in the analyte band being integrated moves across two pixels on the detector array, or to the entire time the portion of the wavelengths of the light signals in the analyte band being integrated is in the detection zone, or to any time therebetween. In addition, the portion of the wavelengths of the light signals in the analyte band being integrated can, according to various embodiments, include (1) a range of wavelengths about a peak intensity of the light signals extending over two pixels of the detector array; or (2) a range of wavelengths including all wavelengths of the light signals, or (3) a range of wavelengths anywhere between (1) and (2) above. By way of example, the integration time can include a time it would take for the detector to integrate a range of wavelengths of the analyte band corresponding to a full width of the intensity curve of the light signals in analyte band at half of the peak or maximum intensity of the intensity wire, or to its "full width at half max." The portion of the wavelengths of the light signals in the analyte band being integrated can depend on the number of different colors being integrated, and on how well the colors are separated from one another in the emission spectra. As a general rule, the better separated the colors in the emission spectra, the wider the portion of the wavelengths of the light signals, and, hence, the longer the effective integration time. In the context of various embodiments, the "effective integration time of an analyte band" therefore, as defined above, corresponds to the integration time for a portion of the wavelengths of the light signals in the analyte band, where the portion can include all of the wavelengths or a range thereof.

According to various embodiments, the use of TDI in collecting data points among other things addresses the problem of lowered irradiance when using irradiation sources emitting non-coherent light, such as LED's. The irradiance, that is, photons emitted per millimeters squared, is typically about a thousand times lower in LED's when compared with the irradiance of lasers. TDI, according to the present invention, among other things addresses the problem of lowered irradiance by allowing a longer period of time for the integration of signals from excited markers. Related to TDI is the use of a broad detection zone according to the present invention. In a non-TDI detection system, the detection zone is typically about one tenth of a millimeter squared. When using TDI according to various embodiments, the detection zone for one channel can be one hundred times larger, that is, about one millimeter squared, allowing a relatively larger number of markers to be excited and a larger number of data points to be integrated into a detector. The above principle of various embodiments can be equally applicable in instances where a plurality of channels are used, the detection zones of each of the respective channels being adapted to be irradiated by at least one irradiation source emitting non-coherent light.

For the purpose of accumulating charges to effect TDI, instead of shifting the charges on the CCD as a function of the migration of the analyte bands, various embodiments encompass within its scope moving the CCD itself and/or the image itself, that is, the light signals from the detection zone, as a function of migration of the analyte bands such that the result of such movement is the tracking of each analyte band by a continuously moving row of accumulating photogenerated charge on the CCD during the effective integration time of the analyte band. By way of example, to accomplish the desired result mentioned above, appropriate motors, gearing, belt drives, control units and power supplies can be used. For example, a linear actuator can be used to translate the re-imaging optical system 30 and/or the CCD itself to minimize blurring. The image can in this way be made to be stationary on the CCD throughout the integration time. In such a case, a frame transfer CCD can be used. A frame transfer CCD has a parallel register that can be composed of two CCD's arranged in tandem. The CCD register adjacent to the serial register, or the storage array, is covered with an opaque mask and provides temporary storage for charges during readout. The other CCD register, or the image array, identical in capacity to the storage array, is used for imaging. After the image array is exposed to light, the resulting charges are rapidly shifted in the parallel register up to the storage array for subsequent readout. This shift operation typically takes a millisecond. While the masked storage array is being read, the image array may integrate charge from the next image. See Charge-Coupled Devices for Quantitative Electronic Imaging, Photometrics Ltd. (1992), the content of which is incorporated herein in its entirety by reference.

Referring now to FIGS. 4, 5a and 5b, according to various embodiments, instead of one irradiation source, a plurality of irradiation sources can be provided to excite marker compounds in a sample. In the embodiment shown in FIGS. 4-5b, the irradiation sources comprise four LED's 50, 52, 54 and 56, the LED's being positioned so as to irradiate channel-defining member 58, which defines two channels in the form of two capillary tubes as shown in particular in FIG. 5b. Each LED emits non-coherent light in a predetermined range of wavelengths. For example, LED 50 and LED 52 emit substantially blue light, LED 54 emits substantially green light, and LED 56 emits substantially yellow light. As the above example shows, multiple LED's can be used to increase the available light. For example, if LED's 50 and 52 emit blue light, they can be used simultaneously, either continuously or in a pulsed fashion, in this way increasing the amount of available blue light to obtain a proportional response in the associated markers. Although each type of marker used may ideally be excited by a different wavelength, LED's of the optimum wavelength and power level may not be available for each given application. Hence, different markers may use the same LED.

The modulating optics according to the above embodiment of the present invention shown in FIGS. 4, 5a and 5b are comparable to the modulating optics in the embodiment shown in FIG. 1, with like components having been labeled with like reference numerals. Thus, for each irradiation source, a conditioning filter 18 and a optical component for focusing 19 are provided, it being understood that the respective conditioning filters and focusing lenses for the respective irradiation sources are not, however, necessarily identical merely by virtue of the fact that they have been labeled with like reference numerals. As previously noted with respect to FIG. 1, the function of each conditioning filter 18 is to let through only light in the wavelength range of excitation light for one or more of the markers. The conditioning filters 18 each substantially block predetermined ranges of wavelengths of light emitted by the corresponding LED. The predetermined ranges correspond to wavelengths of light that can overlap with the emission spectra of the markers being excited by the corresponding LED. The function of each optical system 19 for focusing is to focus the conditioned light from the conditioning filter onto the detection zone 14, which, in the embodiment of FIGS. 4, 5a and 5b, corresponds to a respective detection zone for each of the shown capillary tubes. Excited markers in detection zone 14 thereafter emit light signals in the form of emitted light 22. The light from the detection zone, as in the case of the first-mentioned embodiment of the present invention described in relation to FIG. 1, includes the emitted light 22, and, in addition, a portion of the conditioned light 20 passing through the detection zone.

According to various embodiments, the light from the detection zone, labeled 20 and 22 in FIG. 5a, can be collimated by collimating optical system 24. The light thus collimated is thereafter passed through a corresponding bandpass filter 50' on filter wheel 60 as shown in broken lines in FIGS. 5a and 5b. It is noted that the filters in FIGS. 5a and 5b have been shown in phantom (broken lines) because, in those figures, the depiction of the filter wheel 60 is not cross-sectional, but rather represents plan views thereof.

Referring to FIG. 4, the filter wheel is shown in more detail as supporting therein a plurality of bandpass filters 51, 53, 55, and 57. Each of the bandpass filters is adapted to let through, substantially exclusively, predetermined wavelengths of light from the detection zone corresponding to a portion of the wavelengths of the light signals emitted by an associated marker. According to various embodiments, there is a bandpass filter provided for each associated marker. The portion of the wavelengths of the light signals can include all of the light signals, or it can include, for each marker, a range of wavelengths about the peak intensity of light signals. For example, the range of wavelengths about a peak intensity of emitted light signals can be between about 5% to about 20% of wavelengths on each side of the peak for a given marker, or it can include the range of wavelengths at about half of the intensity of the peak, generally called "full width at half max." Thus, by way of example, bandpass filter 51 is adapted to filter therethrough light signals emitted by given markers responsive to LED 50. In FIGS. 5a and 5b, the apparatus according to various embodiments is depicted in a mode where LED 50 irradiates the detection zone 14. However, it is clear that any of the shown LED's can be selectively used to irradiate the detection zone 14. The filter wheel 60 (FIG. 5a) can be actuated by a filter wheel mechanism 62 (FIG. 5a) that controls the filter wheel to selectively position, in the path of the collimated light, the bandpass filter corresponding to the marker excited by the active LED, that is, by the LED being used to irradiate the detection zone. Filter wheel mechanism 62 may be controlled by a microprocessor or other similar device (not shown) as would be recognized by one skilled in the art. Similar to the embodiment in FIG. 1, the thus filtered light is focused by a re-imaging optical system 30 onto an array 34 of solid-state detectors or detector array 34 such as onto the photo-detecting surface of the parallel register of a charge-coupled device such as CCD 32. It is to be noted that various embodiments can include within its scope the provision of a single LED to excite all markers, the provision of multiple LED's to excite given ones of the markers and the use of one LED per marker, the selection and number of bandpass filters being a function of the markers themselves.

As seen more clearly in FIG. 4, the filter wheel according to various embodiments can further include a filter thereon adapted to let through only light signals from the capillaries generated by a fifth marker. Four markers can be used to label the moving analytes where the analytes are DNA fragments, each marker corresponding to a given one of the bases in a DNA chain, that is, to the purines A (adenine) and G (guanine) and to the pyrimidines C (cytosine) and T (thymine). In addition, according to various embodiments, a fifth marker can, for example, be used for fragment analysis of the analytes. The fifth marker may be any marker, such as a dye marker, for doing fragment analysis. It is to be noted that, according to various embodiments, the number of markers that can be used are not limited to four or five as stated in the above example, but are rather limited only by the number of dyes available on the market and responsive to the irradiation source or sources being used, based on application needs. Fragment analysis can be accomplished using, for example, the GENESCAN® Analysis software produced by Applied Biosystems, Inc., Foster City, Calif. The GENESCAN® Analysis software calculates the size of the unknown analytes by generating a calibration or sizing curve based upon the migration times of the analytes in a standard that have been labeled with a marker. The unknown analytes are mapped onto the curve and converted from migration times to sizes. In the case of the embodiment shown in FIG. 4, the fifth marker filter FD on filter wheel 60 lets through light signals corresponding to markers used to label analytes in the standard. These markers are excitable by at least one of the irradiation sources 50, 52, 54, and 56 appropriately mounted to allow fragment analysis.

Referring now to FIGS. 6a through 6e, these figures depict images produced by moving analyte bands on the detector array 34 of CCD 32 shown in the embodiment of FIGS. 4, 5a and 5b. Images are shown for each of the markers used to label the analytes and which are responsive to excitation by a given one of the irradiation sources 50, 52, 54, and 56. Each shown frame of photo-detecting surface 36 in FIGS. 6a through 6e shows two lanes of analyte bands each corresponding to one of the two capillaries of channel-defining member 58. The bands move along the direction of migration M, and are shown as being limited on each side thereof in the spectral direction by virtue of the light from the markers having been filtered through a corresponding bandpass filter. At the right of each frame is shown an intensity profile 45 corresponding to the capillary for which the charges are produced on photo-detecting surface 36 on the right lane thereof.

According to various embodiments, the intensity profiles are, according to known methods, aligned and combined, and thereafter can be multicomponented in order to account for any spectral overlap. Similar to the embodiment of FIG. 1, the serial register of the CCD 32 in the embodiment of FIGS. 4, 5a, and 5b collects the charges accumulated for each analyte band during its integration time. All signals received from the detector can be converted from analog to digital and conveyed to a serial port for transmission to a multipurpose computer for storage and for further processing and analysis. Alternatively or additionally, the analog output could be sent directly to an output device for display or printing. By way of example, a multipurpose computer may be used to perform the multicomponenting process. Multicomponenting is a process that is known to a person skilled in the art, and that can involve a spectral calibration within a multicomponenting software program. The spectral calibration can be obtained through a predetermined signature matrix corresponding to each marker. Each signature matrix provides a signature snapshot of the intensity of light signals by a given marker as a function of the wavelengths of those light signals. By virtue of the signature matrices, a combination of intensity curves for a given wavelength band emitted from the detection zone can be broken down into its components corresponding to light signals emitted by individual ones of the markers. In this way, a relatively accurate assessment of the light signals by respective ones of the markers can be made for the detection process.

In operation, the apparatus according to the embodiment of the present invention shown in FIGS. 4, 5a, and 5b effects an irradiation of detection zone 14 by each respective one of the irradiation sources, in sequence. The filter wheel is in each case adjusted to dispose before collimating optical system 24 a bandpass filter 51, 53, 55, 57, or FD corresponding to the marker being used. The detection zone can be, according to various embodiments and found in the embodiments shown in FIGS. 4, 5a and 5b, irradiated for the duration of the integration time of the moving analyte bands across the detection zone. During the integration time, similar to the embodiment described in relation to FIG. 1, the charges generated by the light signals for markers being detected can be moved along the parallel register in the direction of migration and are accumulated in the detector or CCD 32 before they are read. Thereafter, another respective one of the irradiation sources is used to irradiate the detection zone to excite corresponding ones of the markers, while a corresponding bandpass filter is positioned before the collimating optical system 24 by filter wheel 60. Again, light signals from the excited markers are detected by detector 32, the charges associated therewith being accumulated in the detector during the integration time before the accumulated charges are read. The above process can continue until all of the irradiation sources have irradiated the detection zone, and until all filters, including filter FD, have been positioned before the collimating lens to filter the light therefrom. Detector 32 can be a frame transfer CCD, such that each frame of the CCD upon which charges have been accumulated can be transferred to a storage array, the image array therefore being available for the next series of charge accumulations produced by the next respective one of the irradiation sources being used.

The above process may be repeated in cycles as many times as necessary in order to obtain sufficient data regarding each analyte being detected. Fewer cycles typically result in an increase in signal. This is because fewer cycles mean longer integration times, and therefore increased readout signals over the noise typically associated with a CCD. On the other hand, increasing the number of cycles can improve the dynamic range of the system. The dynamic range of the system is defined as the largest peak signal that can be read by a given CCD (or "full well capacity") over the smallest peak that can be read by the CCD just above the noise level. A CCD typically has a given full well capacity. If a peak signal is above the full well capacity of a CCD, it will be off the scale of the CCD. Short integration times allow peak signals to be generally attenuated so as to reduce the possibility of saturating the CCD with off-scale signals, that is, with signals that go beyond the CCD's full well capacity. In this way, analyte concentrations may be increased while still allowing the CCD to reliably detect signal levels without saturation. According to various embodiments, there is a trade-off between the use of fewer cycles amounting to longer integration times (such as, for example, 5 seconds) and the use of more cycles amounting to shorter integration times (such as, for example, 1 second). Longer integration times are useful where the noise level is relatively high and where the sensitivity of the system needs to be increased in light of the same. On the other hand, where the noise level in the system is relatively low, multiple reads may be taken of signals from the same marker, and the read signals may thereafter be multicomponented, the CCD in this way allowing the detection of brighter peaks without going off-scale.

By way of example, a frame transfer CCD may be controlled to collect the light signals corresponding to the blue marker during integration time t while the LED exciting primarily the blue marker irradiates the detection zone. Thereafter, the entire CCD is read out. The filter wheel is then switched to the bandpass filter associated with the green marker, and the LED exciting primarily the green marker irradiates the detection zone. The CCD then collects the light signals corresponding to the green marker during integration time t. The entire CCD is then read out. The filter wheel is then switched to the bandpass filter associated with the yellow marker, and the LED exciting primarily the yellow marker irradiates the detection zone. The CCD then collects the light signals corresponding to the yellow marker during integration time t, and the entire CCD is thereafter read out. The above process can then be repeated for all five markers in this example and as described in relation to FIGS. 4, 5a and 5b. As suggested above, in this example, the band takes about five times the integration time from the top of the frame transfer CCD to the bottom thereof, that is, to the readout register. Each readout of the CCD corresponds to one marker. All of the readouts can then be aligned and combined in a known manner for multicomponenting.

An example of the manner in which multicomponenting may be effected is shown in FIGS. 6f through 6h. Here, it is assumed that filters 51, 53, 55, 57, and FD let through wavelengths of light in the blue, green, yellow, red and "fifth" portions of the spectrum. The "fifth" portion may, for example, be in the orange range of the spectrum. FIG. 6f is a schematic representation of an electropherogram showing fluorescence intensity curves for each filter of the filter wheel in FIG. 4 during three readings of the signals by detector 32. The intensity curves correspond to a reading of light signals from an analyte labeled with a marker such as FAM, that is, a dye marker that emits light signals mostly in blue. The first portion of each curve, drawn in solid lines, corresponds to a reading from each one of the blue filter, green filter, yellow filter, red filter and fifth filter of FIG. 4 during a first integration time t for each filter. The second portion of each curve, drawn in broken lines, corresponds to a reading from each of the mentioned filters during a second integration time t. The third portion of each curve, drawn in solid lines, corresponds to readings from each of the mentioned filter during a third integration time t. In the schematic representation of the electropherogram of FIG. 6f, the horizontal axis corresponds to distance traveled by the analyte, and the vertical axis corresponds, for each filter, to the fluorescence intensity of light emerging from that filter. Thus, the first set of curves in solid lines represents intensity curves for light emerging from each filter during a first cycle of the filter wheel 60. The second set of curves in broken lines represents intensity curves for light emerging from each filter during a second cycle of the filter wheel 60. The third set of curves in solid lines represents intensity curves for light emerging from each filter during a third cycle of the filter wheel 60. As seen in FIG. 6f, the light from the blue filter exhibits the most intensity during each cycle, the intensity decreasing as light is collected from the green filter, the yellow filter, the red filter and the fifth filter, respectively. As seen in the instant example, therefore, spectral overlap causes FAM to emit mostly in blue, some in green, less in yellow, etc. As, within each cycle, filter wheel 60 is rotated to place a subsequent filter in the path of fluorescence from the detection zone 14, the analyte has moved a distance x as marked on FIG. 6f after an integration time t.

Referring now to FIG. 6g, that figure is a schematic representation of the intensity curves of FIG. 6f in aligned format for multicomponenting. Here, each intensity curve other than the one corresponding to blue light is shifted by a multiple of x as a function of the filter to be aligned with the intensity curve corresponding to blue light. After being aligned, the intensity curves are combined and multicomponented, thus yielding the intensity curve for FAM shown in FIG. 6h. To the extent that only FAM is being detected in the example of FIGS. 6f through 6h, the intensity curves for JOE, TAMRA, ROX, and the fifth dye are all flat in FIG. 6h, as recognizable by one skilled in the art.

Figure 6I:
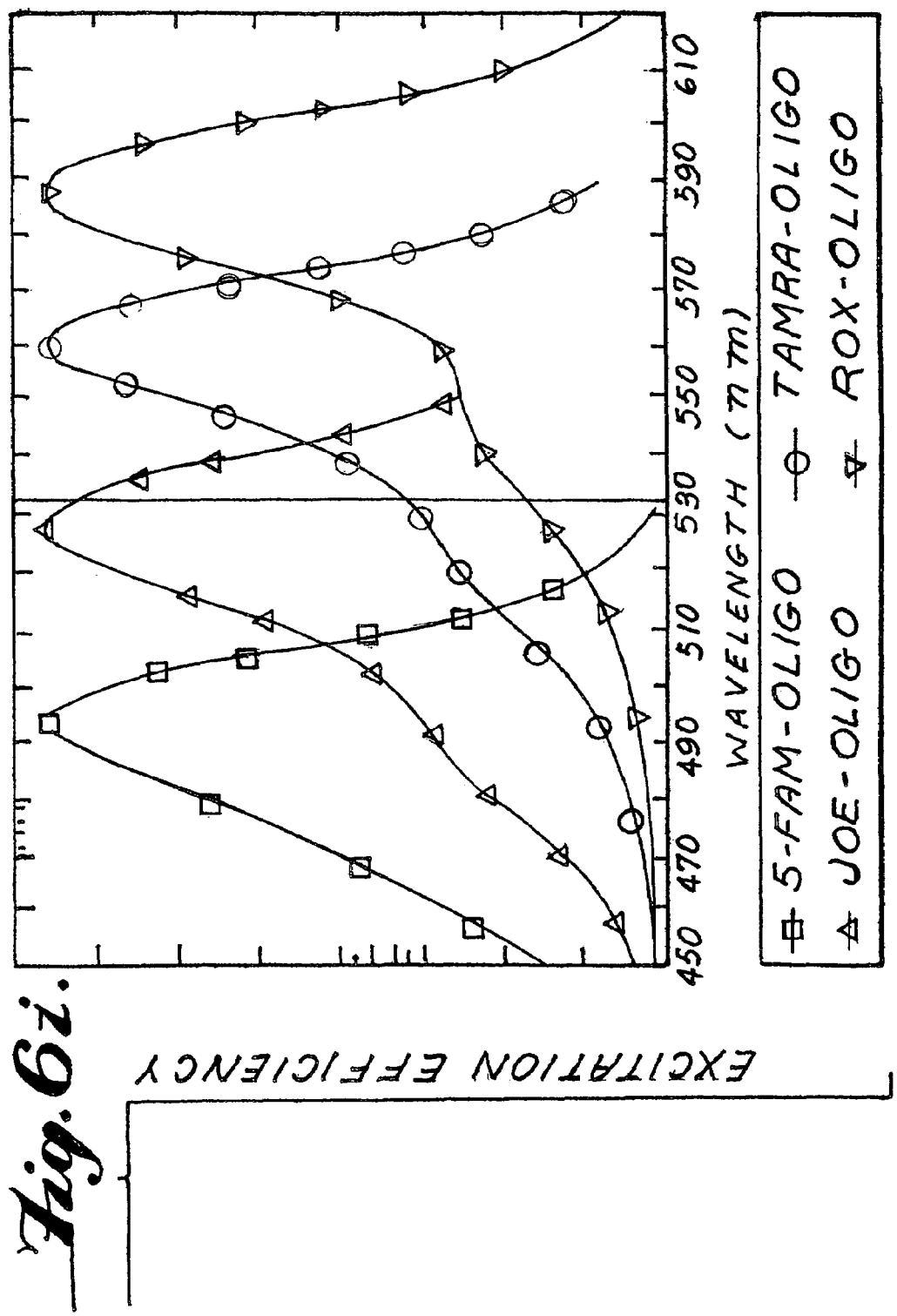
FIG. 6i is a graph of excitation efficiency versus wavelength for four exemplary markers.
Figure 6J:
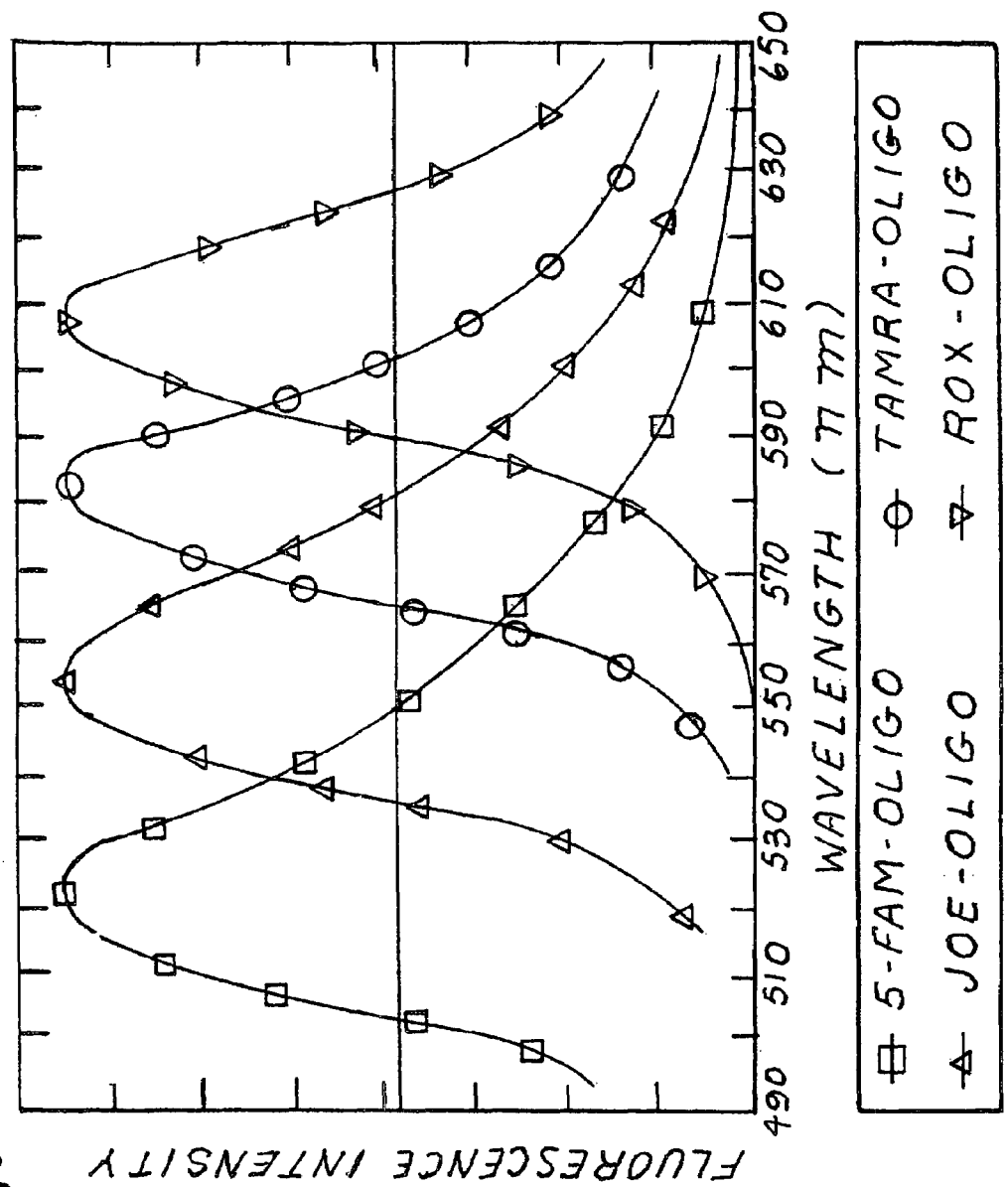
FIG. 6j is a graph of fluorescence intensity versus wavelength for the exemplary markers of FIG. 6i.

Referring now to FIGS. 6i and 6j, representative excitation efficiency curves and fluorescence intensity curves are shown as having been plotted versus wavelength for four different dye markers that can be used in oligosynthesis, namely, 5-FAM, JOE, TAMRA, and ROX. These dye markers are exemplary of those that can be used in various embodiments where a plurality of dye markers are to be used, such as the embodiments shown in FIGS. 4, 5a, 5b, and 7.

As seen in FIG. 6i, the x-axis corresponds to wavelengths, expressed in nanometers or nm, emitted by an irradiation source, and the y-axis corresponds to the percentage of excitation efficiency. Here, it can be easily appreciated that 5-FAM has its maximum absorbance, corresponding to its peak percent excitation efficiency, at about 490 nm. The maximum absorbance at a given wavelength indicates that the dye marker being considered fluoresces at its peak fluorescence intensity when it is irradiated at the given wavelength. As further seen in FIG. 6i, JOE has a maximum absorbance at about 526 nm, TAMRA has a maximum absorbance at about 560 nm, and ROX has a maximum absorbance at 588 nm. The wavelengths on the x-axis could be emitted by any irradiation source, such as, for example, an LED. FIG. 6i also shows that, where a dye marker, such as 5-FAM, is being irradiated at its maximum absorbance wavelength, other dye markers, such as, for example, JOE, TAMRA, and ROX, do exhibit some absorbance, although to a lesser extent when compared to 5-FAM.

Referring now to FIG. 6j, the x-axis corresponds to the wavelengths of fluorescent light, expressed in nm, emitted by excited dye markers. The y-axis corresponds to the percentage of fluorescence intensity. As seen in FIG. 6j, 5-FAM has a peak fluorescence intensity at about 522 nm, JOE has a peak fluorescence intensity at about 554 nanometers, TAMRA has a peak fluorescence intensity at about 582 nm, and ROX has a peak fluorescence at about 608 nm. The wavelengths on the x-axis are emitted by the four mentioned dye markers. FIG. 6j also shows that, where a dye marker, such as TAMRA, fluoresces at its peak fluorescence intensity, other dye makers, such as 5-FAM, JOE, and ROX, also fluoresce, although at lesser fluorescence intensities.

When light is emitted from the dye markers in the detection zone at various colors, each dye marker can be excited efficiently, and further in a way that will allow its detection by way of its unique spectral signature. When two dye markers exhibit fluorescence intensity peaks that are close together, that is, for example, when the difference between the fluorescence intensity peaks of two dye markers is less than about 30 nm, there is a high level of overlap of the light emitted by those two dye markers. A high level of overlap makes it harder to distinguish between the light emitted by the two dye markers, and therefore makes it harder to determine the relative amounts of the two dye markers. Typically, there is usually overlap present in the light emitted by different dye markers, as suggested for example in FIGS. 6i and 6j. However, the overlap can be minimized by selecting dye markers that present easily distinguishable fluorescence intensity peaks, such as those shown in FIG. 6j. According to various embodiments, it is possible to first start with an irradiation source emitting radiation within a given range of wavelengths, and to investigate each such irradiation source to see how well it excites the dye markers available. Graphs such as those shown in FIGS. 6i and 6j could be used in this context. For example, where excitation efficiency curves of various dye markers are plotted in the manner shown in FIG. 6i, an irradiation source, such as an LED emitting light in a given range of wavelengths, can be predicted to excite given ones of the dye markers based on their excitation efficiencies. Thereafter, from a fluorescence intensity graph such as in FIG. 6j, it becomes possible to determine how much overlap would exist between intensity peaks of the different markers. From such a determination, it then becomes possible to choose which set of markers would be best suited for a particular application. Once the dye markers have been chosen, it then becomes possible to choose the filters corresponding thereto, such as the filters shown on the filter wheel of the embodiment FIG. 4 described above, and on the filter wheel in the embodiment of FIG. 7 described below. The best set of markers would exhibit the desired minimum amount of overlap at the emitted wavelengths that are to be detected.

Because each marker has a different excitation curve, the fluorescence output can be dramatically increased by the use of an LED that is well matched to this marker. This provides an increase in the desired light, that is, in the emission from the marker of interest, while minimizing undesired light, that is, background light from the system and emissions from other markers. This results in data that is of better quality. For example, if a blue/green LED with an excitation maximum of 503 nm is used for the marker designated FAM, the absorption will be high for FAM, at about 80%, and low for the marker designated ROX, at about 6%. Similarly, a yellow LED with an excitation maximum of 592 nm will not excite FAM, while its absorption in connection with ROX will be about 90%.

Referring now to FIG. 7, another embodiment is depicted. This embodiment is similar to the one shown in FIGS. 4, 5a, and 5b to the extent that a number of irradiation sources are used to sequentially irradiate the detection zone. However, the embodiment of FIG. 7 differs from the embodiment of FIGS. 4, 5a, and 5b in a number of respects. The premise behind the embodiment of FIG. 7 is to allow a reading of light signals having wavelengths in differing frequency ranges on the same array of the detector, the charges corresponding to the generated light signals being spatially offset as a function of the bandpass filter being used in connection with the markers emitting those light signals. Advantageously, such an embodiment allows a continuous reading of the accumulated charges on the detector array during time delay integration or TDI, rather than a frame-by-frame reading as in the case of the embodiment of the present invention described above with reference to FIGS. 4, 5a, and 5b.

In the embodiment of FIG. 7, the irradiation sources, together with associated optics such as the conditioning filter 18 and the optical system for focusing 19, can be provided on an irradiation source wheel 61 as shown. As seen in FIG. 7, components of the apparatus that are similar to those in the embodiment of FIG. 1 have been labeled with the same reference numerals, such as conditioning filter 18, focusing optical system 19, collimating optical component or system 24, and re-imaging optical component or system 30. The irradiation wheel 61 is rotatable to selectively position each respective one of the irradiation sources and associated optics to irradiate detection zone 14. Four irradiation sources similar to sources 50, 52, 54, and 56 in FIGS. 4, 5a, and 5b, can be provided. In addition, a filter wheel 61' can be provided, similar to filter wheel 60 in FIGS. 4, 5a, and 5b. The rotation of both wheels 61 and 61' can be effected by the provision of a filter wheel drive 62 similar to the filter wheel drive of the embodiment of FIGS. 4, 5a, and 5b described above. According to various embodiments, the two wheels 61 and 61' can further be coupled to one another and to the filter wheel drive 62 by way of a rotatable shaft 63 as shown. It is noted that various embodiments encompass within its scope the provision of a plurality of irradiation sources that are not necessarily provided on an irradiation wheel, or the provision of an arrangement where the two wheels 61 and 61' are not coupled to one another by a shaft, but are rather actuated independently by their own respective wheel drives.

In the embodiment of FIG. 7, the apparatus is provided with an offset system 64, which may be disposed either on the filter wheel 61' in association with a corresponding bandpass filter, or coupled to at least one of the detector 32, the modulating optics, and the detection zone 14, for spatially offsetting the light signals impinging upon the array of the detector by a predetermined amount as a function of the bandpass filter being used. In effect, the offset system is, according to various embodiments, adapted to offset the light signals impinging upon the array 34 of detector (CCD) 32 by a predetermined amount for each bandpass filter. The offsetting may be accomplished by providing an offset system 64 that includes a plurality of offset mechanisms 66, shown in broken lines in FIG. 7, and disposed on filter wheel 61'. Each offset mechanism is associated with a respective one of the bandpass filters to offset the filtered light therefrom. In such a case, the offset mechanisms 66, one of which is shown in FIG. 7, may comprise gratings, mirrors, prisms, or any other devices for offsetting light, as readily recognizable by those skilled in the art. Mechanisms 66 can be distributed about the circumference of filter wheel 61' in front of each corresponding bandpass filter, with wheel 61' in FIG. 7 being otherwise identical to wheel 60 in FIG. 4. In the alternative, the offsetting can be accomplished by providing an offset control device 67, also shown in broken lines, and can be coupled to at least one of the detection zone 14, the modulating optics, and the detector array 34, for offsetting the light signals impinging upon the array 34 of the detector 32. By way of example, the offset system may move at least one of the detection zone 14, collimating optical system 24, re-imaging optical system 30, or detector array 34 by a predetermined amount in order to thereby offset the light signals impinging upon the detector array 34. In this latter alternative of the offset system, the system can include any suitable device for effecting a translational movement of at least one of the detection zone 14, collimating optical system 24, re-imaging optical system 30, or detector array 34, as would be recognized by those skilled in the art. Such devices can include, for example, solenoids, or motor driven linear actuators such as lead screws, rack-and pinion systems, cams, and the like. For example, a cam can be attached to drive shaft 63 to cause a translation of the re-imaging optical system 30 in a number of ways recognizable by one skilled in the art. The predetermined amount can correspond to a one to one ratio relative to the amount by which the light signals impinging upon the detector array are sought to be offset. The range of wavelengths corresponding to the predetermined amount is a function of a number of different factors, such as, for example, the irradiation source being used and the markers being excited. However, once a given set including an irradiation source and its corresponding bandpass filter have been positioned to irradiate the detection zone and to filter light therefrom, the predetermined amount by which the light signals are to be offset may be readily determined by determining where on the detector array the charges produced by those light signals should be situated with respect to the detector array itself, and with respect to light signals in different wavelength frequency ranges. Thus, where individual mechanisms 66 are used in conjunction with a corresponding bandpass filter to offset the light emerging therefrom, each mechanism 66 is chosen according to the frequency ranges of wavelengths that the bandpass filter lets through. In the alternative, where offset control device 67 is used, the offset control may be programmed to offset at least one of the detection zone 14, the modulating optics, and the detector array 34, with respect to one another by the predetermined amount. The offsetting could, by way of example, be accomplished by moving either the detection zone 14, the modulating optics, or the detector array 34, in a translational motion by the predetermined amount, the image created by the light signals being spatially offset correspondingly. The embodiment shown in FIG. 7 can involve the use of a plurality of LED's similar to those used in the embodiment of FIGS. 4, 5a, and 5b. The offset amount should be sufficient be prevent overlap of the images from each bandpass filter.

It is noted that offset system 64, including offset mechanisms 66, or, in the alternative, offset control device 67, are shown in broken lines in FIG. 7 in order to suggest that mechanisms 66 and offset control device may be used as alternatives of the offset system 64. It is further noted that various embodiments encompass within its scope instances where both alternatives, that is, mechanisms 66 and offset control device 67, are used in conjunction with one another. Moreover, the modulating optics, according to various embodiments, comprise at least one of conditioning filter 18, focusing optical system 19, collimating optical system 24, and re-imaging optical system 30, encompasses any devices or system for achieving the functions associated with the components listed above as would be within the knowledge of persons skilled in the art. In addition, with respect to offset control device 67, where the instant disclosure describes a coupling of device 67 to the modulating optics, what is meant is that the offset control device 67 is coupled to at least one of the components of the modulating optics. It is further to be noted that, although the embodiments of FIGS. 1 and 4-5*b* depict a set of two capillaries being analyzed, various embodiments encompass a detection zone defined by any suitable channel-defining member, such as any number of capillaries, any number of channels in an etched plate, and even a slab plate. According to various embodiments, the channel-defining member can assume any orientation according to application needs, such as a horizontal orientation or a vertical orientation. Moreover, the embodiments of FIGS. 4, 5*a*, and 5*b* are not necessarily limited to four irradiation sources and five bandpass filters, but encompass the use of any suitable number of bandpass filters depending on the markers being used. It is further to be noted that, in the described embodiments, any number of different irradiation sources, such as LED's, emitting light in any number of wavelength ranges, may be used. Limitations in this regard may only be a function of the available space, the availability of LED's, and/or the types of markers that can be used. Additionally, whenever an "optical system" is referred to, this system may be a single lens, a lens system, a mirror system, or any other optical system capable of fulfilling the desired and stated functions, as readily recognizable by those skilled in the art.

In operation, the detection zone 14 in FIG. 7 is irradiated by a first one of the irradiation sources, such as, by LED 50 as depicted in FIG. 7. The light signals emitted by the markers excitable by the light from LED 50 are, as previously described, filtered through a corresponding bandpass filter 51, and thereafter focused onto detector array 34 by a re-imaging optical system. Where offset system 64 includes mechanisms 66, the filtered light from bandpass filter 51 is offset by mechanism 66 by the predetermined amount corresponding to the range of wavelengths that the bandpass filter lets through, as described above. Each subsequent irradiation source and corresponding bandpass filter are then positioned to irradiate the detection zone and to filter the light therefrom through a rotation of the wheels 61 and 61' in conjunction with one another. As previously suggested, any number of markers, bandpass filters and LED's may be used in the shown system.

In the embodiment of FIG. 7, charges are accumulated for each respective irradiation source during the integration time of analyte bands excitable by light from the respective irradiation source. The accumulation of charges may be effected, as previously described, either by shifting the charges on the detector array, and/or by moving, relative to one another, the detector array and light signals from the detection zone. After each integration time, the wheels 61 and 61' are rotated to position the next set, including an irradiation source and a bandpass filter, in a functional position, that is, in a position for the irradiation source to irradiate the detection zone and for the bandpass filter to filter the light from the detection zone. The above is carried out until one cycle is completed, that is, until all of the irradiation sources and filters have been used. The above cycle may be repeated as many times as necessary on an application-by-application basis. To the extent that the embodiment of FIG. 7 includes an offset system for spatially offsetting light signals in differing frequency ranges, the embodiment allows a continuous reading of accumulated charges by the detector, thereby making possible a continuous time delay integration of the light signals from the analytes in a sample into the detector array 34. Unlike the embodiment of FIGS. 4, 5*a*, and 5*b*, where the accumulated charges corresponding to each range of wavelengths of light signals are read and discarded before charges for the next range of wavelengths are read, the embodiment of FIG. 7 allows the accumulated charges from each wavelength range to be read in a continuous fashion.

Referring now to FIG. 8, the image produced by the moving analyte bands on the array of detector (CCD) 32 is shown for each of the wavelength ranges and each of the two capillaries 58. In the shown image, each range of wavelengths is assigned an arbitrary color, the ones shown therefore being arbitrarily referred to as "blue," "green," "yellow," "red," and "fifth." For each color, the column on the left corresponds to charges produced by light signals from one capillary, and the column on the right to charges produced by the next capillary. As shown, the array features charges generated by light signals across the color axis λ, offset with respect to one another by offset system 64 in the manner previously described. Although in the shown embodiment, five arbitrary colors are given by way of example, the number of wavelength ranges used will be dependent on the particular application, and can range from one to as many as the system supports. It is noted that the λ axis is referred to here as the "color axis" rather than the "spectral axis," because there is no need for the colors, one for each bandpass filter, to be arranged from shorter to longer wavelengths. According to the embodiment as shown in FIG. 7, to the extent that charges from light signals of differing wavelengths may be produced on the same array of light signals so as to be spatially offset with respect to one another, as seen in FIG. 8, those charges may be accumulated during the integration time and read by the detector on a continuous basis. This eliminates the need to take the time to shut off the detector in order to allow a reading of charges in a given range of wavelengths on a frame-by-frame basis, and/or eliminates the need for a frame transfer CCD. In addition, the above embodiment facilitates a longer integration time, simpler data output and a less complex CCD.

According to various embodiments, the detection zone, including one or more channels, or a slab gel, may be irradiated with multiple-color irradiation sources, such as multiple-color LED's. As in the embodiments of FIGS. 1 and 4-5*b* described above, the use of multiple-color LED's can greatly improve the absorption efficiency of some of the markers. The potential problem that would need to be overcome with such an arrangement would be the elimination of excitation light. Long pass filters or wide band pass filters are conventionally used to reject the excitation light, but only with irradiation sources such as laser sources. According to various embodiments, the irradiation source is conditioned to provide only a narrow wavelength range of light and a bandpass filter is used to substantially block all of the unwanted excitation light. An example of the results, in the form of graphs, of implementing such an embodiment of the present invention is provided in FIGS. 9*a* through 9*d*.

As depicted in FIGS. 9*a* through 9*d*, a detection zone of an apparatus has been irradiated by two irradiation sources simultaneously, although any number of irradiation sources is possible according to various embodiments. In such a case, a set-up of the system may be used such as the one shown in FIG. 1, except that the single LED in FIG. 1 is replaced with a set of double LED's, the associated optics being altered accordingly. In particular, for each set of double LED's, a conditioning filter is used. Here, the conditioning filter has the role of substantially blocking predetermined ranges of wavelengths of light emitted by the LED as previously described, each predetermined range corresponding to each LED, as suggested, for example, in FIG. 9a. FIG. 9a shows a graph of relative excitation intensity for each LED, versus wavelength expressed in nm. The graph of FIG. 9a suggests that two LED's are being used, respectively, generally in the violet and orange portions of the spectrum. However, it is to be understood that various embodiments are not limited to the above two types of LED's, but encompasses any number of LED's emitting light in any range of frequencies according to application needs. As seen in FIG. 9b, each predetermined range that passes through the conditioning filter corresponds to wavelengths emitted by each example of the LED depicted in the graphs, and capable of exciting the markers responsive to each LED. FIG. 9b is a graph of percent transmission of light through the conditioning filter versus wavelength. The behavior of the conditioning filter corresponding to the graphs of FIGS. 9a-9d substantially blocks all excitation light except for sections around the LED emission maximum. Wavelength ranges correspond to a range of from about 450 nm to about 490 nm, and to another wavelength range of from about 580 nm to about 605 nm, as depicted in FIG. 9b. Again, it is noted that the conditioning filter, and the predetermined ranges passing therethrough, are, among other things, functions of the LED set being used, and, to the extent that any number of LED's may be used emitting light in any ranges of frequencies, the conditioning filter is chosen accordingly.

It is further to be noted that the conditioning filter of various embodiments may include a single conditioning filter, or a series of conditioning filters capable of filtering the light from the LED's as previously described. The conditioned light is, as previously described above in relation to FIGS. 1 and 7, focused onto the detection zone of an electrophoretic detection system. The light emitted by markers in the detection zone is then passed through a bandpass filter. The function of the bandpass filter is to let through, substantially exclusively, predetermined wavelengths of light from the detection zone corresponding to a portion of the wavelengths of the light signals emitted by an associated set of markers, to thereby produce filtered light. The bandpass filter's function is to let through only a portion of the light emitted by an associated set of markers, and not the excitation light by the LED's that passes the detection zone. The portion of the wavelengths of the light signals can include all of the light signals, or it can include, for each marker, a range of wavelengths about the peak intensity of light signals. For example, the range of wavelengths about the peak intensity of light signals can be between about 5% to about 20% of wavelengths on each side of the peak wavelength of a given marker, or it can include a range of wavelengths at about half of the intensity of the peak wavelength, or "full width at half max." The collection of the predetermined wavelengths can be performed using a dispersion approach, such as the approach shown in FIG. 1, or by additional bandpass filters as shown in FIG. 4.

As seen in FIG. 9c, where percent light transmission is plotted versus wavelength, the particular bandpass filter being used, the behavior of which is shown in the figure, lets through light corresponding to the "blue," "green," "yellow," "red," and "orange" markers. The regions or zones corresponding to the excitation light by the LED's are blocked. As noted previously with respect to the conditioning filter, the bandpass filter in various embodiments may include a single bandpass filter, or a series of bandpass filters capable of filtering the light from the LED's as previously described.

FIG. 9d plots relative emission intensity versus wavelength, expressed in nm, for the light let through by the bandpass filter. FIG. 9d, in effect, provides a breakdown, by wavelength, of the light transmitted through the bandpass filter. As shown in FIG. 9d, the markers being excited by the LED's used in the example of FIGS. 9a through 9d emit light in the "blue," "green," "yellow," "red," and "orange" ranges of wavelengths. Before focusing the light signals thus filtered onto the detector array of a CCD, a dispersion element can be used, such as grating 28 shown in FIG. 1. In such a case, the resulting image would be similar to that in FIGS. 2 and 3, except that the image will have one or more dark zones corresponding to the blocked excitation light. The existence of one or more dark zones, however, does not prevent the ability to perform multicomponenting to determine the intrinsic dye concentrations of each band in an electropherogram. Accordingly, this embodiment of the present invention that would generate graphs such as those of FIGS. 9a-9d allows the use of multiple-color LED's. TDI can still be performed in any of the previously described manners.

Figure 10:
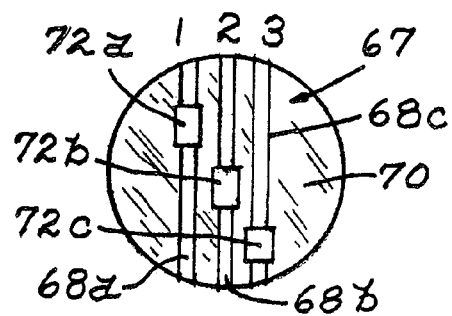
FIG. 10 is a schematic, top-plan view of an irradiation zone showing three channels having been selectively masked to present respective windows according to another embodiment of the present invention.
Figure 11:
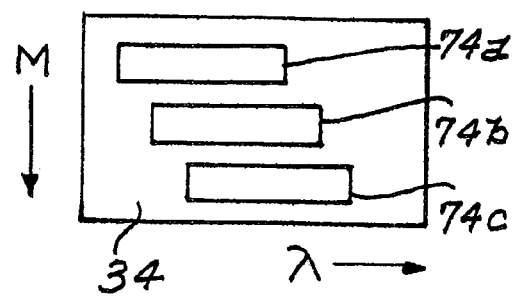
FIG. 11 is a schematic view of a detector array, the detector array having been separated into respective frames for use with light signals emitted from the respective windows of the channels in FIG. 10.

When irradiating multiple-channels with multiple-color LED's, according to various embodiments, the channels may be selectively masked in order to keep the light signals generated by the markers in each channel separate from one another. As seen by way of example in FIGS. 10 and 11, where three channels 68a, 68b, 68c are provided, the channels are selectively masked using a mask 70 to create three windows 72a, 72b, and 72c in the irradiation zone 67. The mask can be made of a metallized surface on a glass or fused silica plate that is disposed adjacent, for example, immediately above the channels. The metal can be deposited in a controlled manner by photolithography methods, as readily recognizable by one skilled in the art of micro-machining to cover the entire plate except in the areas forming the windows. Alternatively, windows can be cut out of an optically non-transparent plate, or a plate with windows can otherwise be formed. As seen in FIG. 11, the array 34 of the detector is configured such that it is divided into three frames 74a, 74b, and 74c, respectively, corresponding to windows 72a, 72b, and 72c, for allowing TDI to be effected on the charges generated by light signals detected through the respective windows on a window-by-window basis.

Figure 12A:
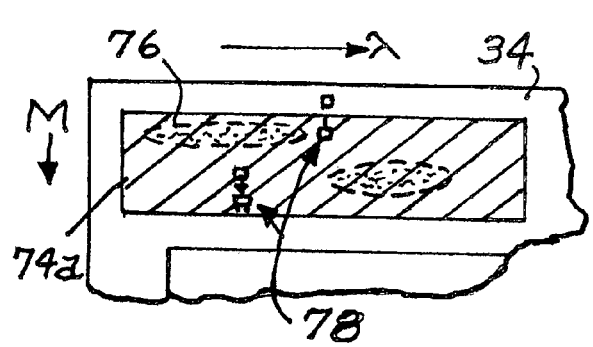
FIG. 12a is a partially cut away view of one of the frames of the detector array shown in FIG. 11.
Figure 12B:
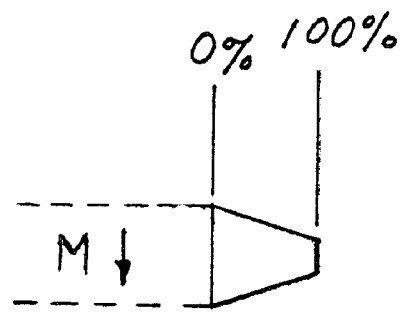

The above concept is more fully illustrated in FIG. 12a, where a frame is partially cut-away to show a schematic representation of the portion of detector array 34 corresponding to frame 74a for detecting light passing through window 72a. Here, each band 76 moves in the migration direction M, and the charge packets on the detector array 34 are accumulated. The accumulation of the charges for effecting TDI may, as described above, be brought about by a shifting of the charges on the detector array in the migration direction M at a predetermined speed corresponding to the average speed of migration of the analyte bands, as suggested in FIG. 12a by the shifting movements depicted by reference numeral 78. Data can be collected from frame 74a from the top of the frame to the bottom of the frame. Some of the light is blocked by the mask, causing a variable collection efficiency as suggested by FIG. 12b. The integration of the accumulated charges occurs in the embodiment of the present invention shown in FIGS. 10-12b on a frame-by-frame basis as previously explained in relation to FIGS. 4, 5a, and 5b, the frame data being combined in a known manner to create an electropherogram. It is further possible, according to various embodiments, to abut the frames, that is, to eliminate any distance between them so as to combine the resulting images on detector array 34. According to various embodiments, the above arrangement can allow the separation and detection of light signals from multiple-channels while permitting the simultaneous irradiation of those channels with multiple-color irradiation sources. The above is made possible through the use of a single camera instead of one camera per channel, the single camera maintaining a spatial separation of light signals from each masked channel.

According to various embodiments, the modulating optics that can be used in the electrophoresis arrangements are disclosed in U.S. application Ser. No. 09/564,790, the content of which is incorporated herein in its entirety by reference. In particular, in the above-referenced application, the modulating optics shown in FIG. 1, using the cat's eye aperture of FIG. 24, can be useful in electrophoresis arrangements according to the various embodiments.

Various embodiments can further pertain to an apparatus for detecting analytes in a sample, and can comprise: means defining at least one channel therein having a detection zone; means for separating a sample containing analytes and disposed in contact with a migration medium disposed within the at least one channel into analyte bands migrating along the at least one channel, wherein each analyte band is detectable by the presence of a marker; means for irradiating the detection zone with non-coherent radiation, that can thereby excite markers responsive to the radiation and which emit light signals indicative of corresponding analytes; means for detecting the light signals by collecting the light signals that can thereby produce charges corresponding to the light signals; means for effecting a time delay integration of the light signals within the detector array by accumulating within the detector array the charges corresponding to light signals associated with at least one given analyte band during an integration time of the at least one given analyte band moving across the detection zone; and means for reading the accumulated charges. The above-described means have been substantially shown and described in FIGS. 1 through 15.

It is to be understood that various embodiments are useful in detecting and imaging not only fluorescent labeled molecules, but also proteins, virus, bacteria, etc., which are electrophoretically or otherwise separated on a variety of carriers, such as in capillary tubes, and across, on, in, or through slab gels, membranes, filter paper, petri dishes, glass substrates, and the like.

Other embodiments of the present teachings will be apparent to those skilled in the art from consideration of the present specification and practice of the present teachings disclosed herein. It is intended that the present specification and examples be considered as exemplary only with a true scope and spirit of the teachings being indicated by the following claims and equivalents thereof.

What is claimed is:

1. An apparatus for detecting analytes in a sample, comprising:
   one or more channels having a detection zone;
   one or more irradiation sources disposed for irradiating the detection zone with radiation;
   a detector array disposed for collecting light signals emitted from markers in the detection zone excited by the radiation, the detector array having an output; and
   a system coupled to the detector array for effecting time delay integration of charges on the detector array corresponding to the light signals by accumulating the charges before reading the charges at the output of the detector array, the system effecting time delay integration by moving, relative to one another, the detector array and the detection zone such that the detector array tracks light signals emitted from the markers.

2. The apparatus according to claim 1, wherein the system for effecting time delay integration accumulates the charges by at least one of (a) shifting the charges on the detector array, and (b) moving, relative to one another, the detector array and light signals from the detection zone.

3. The apparatus according to claim 1, wherein the one or more irradiation sources comprises one or more light emitting diodes.

4. The apparatus according to claim 1, further comprising modulating optics disposed between the detection zone and the detector array, the modulating optics comprising a relay lens system having a collimating lens and a re-imaging lens.

5. The apparatus according to claim 4, wherein the modulating optics further include a conditioning filter disposed between the one or more irradiation sources and the detection zone.

6. The apparatus according to claim 5, wherein the modulating optics further include a focusing lens disposed between the conditioning filter and the detection zone.

7. The apparatus according to claim 4, wherein the modulating optics further include a transmission grating disposed between the focusing lens and the re-imaging lens.

8. The apparatus according to claim 4, wherein the modulating optics further include a filter disposed between the detection zone and the detector array for filtering through only the light signals.

9. An apparatus for detecting analytes in a sample, comprising:
   one or more channels having a detection zone;
   one or more irradiation sources disposed for irradiating the detection zone with radiation;
   a detector disposed for collecting light signals emitted from markers in the detection zone excited by the radiation, the detector having an output;
   modulating optics disposed between the detection zone and the detector; and
   a system coupled to the detector for effecting time delay integration of the charges on the detector corresponding to the light signals by accumulating the charges before reading the charges at the output of the detector, the system effecting time delay integration by moving one or more of the detection zone, the modulating optics, and the detector.

10. The apparatus of claim 9, further comprising a re-imaging lens disposed between the detection zone and the detector array for optically inverting an image produced by the light signals before the image is collected by the detector array.

11. An apparatus for detecting analytes, comprising:
   a plurality of elongate channels;
   a light source;
   an excitation-light pathway extending from said light source to said channels;
   focusing optics disposed along said excitation-light pathway; and
   a charge-coupled device optically coupled to said channels,
   wherein said charge-coupled device is configured to operate in time-delay integration mode by moving the charge-coupled device to track an emission signal.

12. The apparatus of claim 11, wherein said channels are defined by capillary tubes or grooved plates.

13. The apparatus of claim 11, further comprising a separation medium supported by said channels.

14. The apparatus of claim 11, including at least four co-extensive channels.

15. The apparatus of claim 11. further comprising modulating optics disposed along an optical path extending between said charge-coupled device and said channels.

16. The apparatus of claim 11, wherein said light source is a light-emitting diode.

17. An apparatus for detecting analytes, comprising:
a plurality of elongate channels;
a detection zone located at one or both of (i) along said channels and (ii) outside of said channels;
a light source and associated focusing optics configured for irradiating at least a portion of said detection zone with light; and
a charge-coupled device optically coupled to said detection zone for collecting light signals emitted from markers in the detection zone excited by the light irradiated by the light source;
wherein said charge-coupled device is configured to operate in time-delay integration mode, the apparatus effecting time delay integration by moving, relative to one another, the charge-coupled device and the detection zone such that the charge coupled device tracks light signals emitted from the markers.

18. The apparatus of claim 17, wherein said detection zone is located along said channels.

19. The apparatus of claim 17, wherein said detection zone is located outside of said channels.

20. The apparatus of claim 17, including at least four co-extensive channels.

21. The apparatus of claim 17, further comprising modulating optics disposed along an optical path extending between said CCD and said detection zone.

22. The apparatus of claim 17, wherein said light source is a light-emitting diode.

23. An apparatus for detecting analytes, comprising:
a plurality of analyte-migration lanes;
a light source;
an excitation-light pathway extending from said light source to said analyte-migration lanes, with said light source being disposed to direct light along said excitation-light pathway;
a charge-coupled device configured to operate in time-delay integration mode and configured to receive light signals from the plurality of analyte-migration lanes; and
a fluorescence-emission pathway optically coupling said analyte-migration lanes and said charge-coupled device;
modulating optics disposed between the plurality of analyte-migration lanes and the charge-coupled device; and
a system coupled to the charge coupled device for effecting time delay integration by moving one or more of the analyte-migration lanes, the modulating optics, and the charge-coupled device.

24. The apparatus of claim 23, including at least four co-extensive analyte-migration lanes.

25. The apparatus of claim 23, further comprising modulating optics disposed along one or both of said excitation-light and fluorescence-emission pathways.

26. The apparatus of claim 23, wherein said light source is a light-emitting diode.

27. An apparatus for detecting analytes in a sample, comprising:
one or more channels including one or more detection zones;
one or more irradiation sources, each irradiation source being capable of irradiating with radiation at least one of the one or more detection zones;
a detector array disposed for collecting light signals emitted from the one or more detection zones by markers excited by the radiation, the detector array being capable of generating one or more output signals; and
a charge-shifting system coupled to the detector array for effecting time delay integration of charges on the detector array which correspond to the light signals, the charge-shifting system being capable of accumulating the charges on the detector array and moving the detector array at a speed substantially synchronized to respective speeds of migration of bands of markers that migrate across the one or more detection zones, to track an emission signal.

28. The apparatus of claim 27, wherein the charge-shifting system is capable of synchronizing prior to the detector array generating the one or more output signals.

29. An apparatus for detecting analytes in a sample, comprising:
a plurality of channels, each channel including one or more detection zones;
one or more irradiation sources, each irradiation source being capable of irradiating with radiation at least one of the one or more detection zones;
a detector array disposed for collecting light signals emitted from the detection zone by markers excited by the radiation, the detector array being capable of generating one or more output signals;
masks to selectively mask the plurality of channels such that light signals from each of the plurality of channels are kept separate from light signals from others of the plurality of channels; and
a system coupled to the detector array for effecting time delay integration of the charges on the detector array which correspond to the light signals by accumulating the charges before reading the charges at the output of the detector array, the system being capable of effecting time delay integration by moving, relative to one another, the detector array and light signals from the detection zone, the system comprising a charge-shifting system capable of shifting accumulated charges corresponding to light signals emitted from the one or more detection zones.

30. The apparatus of claim 29, wherein the detector array comprises a CCD.

31. The apparatus of claim 29, wherein the system for effecting time delay integration moves one or more of the detection zone, the modulating optics, and the detector.

32. The apparatus of claim 29, wherein the charge-shifting system is capable of shifting accumulated charges corresponding to light signals emitted from the one or more detection zones at a speed substantially synchronized to speeds of migration of bands of markers that migrate across the one or more detection zones.

* * * * *